United States Patent
Shelley, Jr. et al.

(10) Patent No.: US 8,853,634 B2
(45) Date of Patent: Oct. 7, 2014

(54) RESIN DETECTION SYSTEM

(75) Inventors: Paul H. Shelley, Jr., Lakewood, WA (US); Paul G. Vahey, Seattle, WA (US); Gregory James Werner, Puyallup, WA (US); Gabor John Kemeny, Middleton, WI (US); Gard Groth, Madison, WI (US); Gina Elaine Stuessy, Madison, WI (US); Natalie Ann Crothers, Wisconsin Dells, WI (US)

(73) Assignee: The Boeing Company, Chicago, IL (US)

( * ) Notice: Subject to any disclaimer, the term of this patent is extended or adjusted under 35 U.S.C. 154(b) by 168 days.

(21) Appl. No.: 13/418,064

(22) Filed: Mar. 12, 2012

(65) Prior Publication Data

US 2013/0234030 A1    Sep. 12, 2013

(51) Int. Cl.
*G01J 5/02*    (2006.01)

(52) U.S. Cl.
USPC ............................................... 250/353

(58) Field of Classification Search
CPC .................................................. G01N 25/72
USPC ............................ 250/353, 338.1–338.5, 340
See application file for complete search history.

(56) References Cited

U.S. PATENT DOCUMENTS

| | | | | |
|---|---|---|---|---|
| 3,949,225 A | * | 4/1976 | Aguilera | 250/334 |
| 5,748,389 A | * | 5/1998 | Gering et al. | 359/811 |
| 6,594,600 B1 | * | 7/2003 | Arnoul et al. | 702/94 |
| 6,903,339 B2 | | 6/2005 | Shelley et al. | |
| 7,223,977 B2 | | 5/2007 | Shelley et al. | |
| 2009/0287429 A1 | * | 11/2009 | Calcaterra et al. | 702/57 |

FOREIGN PATENT DOCUMENTS

| | | | |
|---|---|---|---|
| EP | 1011086 A2 | | 6/2000 |
| JP | 09062839 A | * | 3/1997 |
| JP | 11077805 A | | 3/1999 |
| JP | 2003279325 A | * | 10/2003 |

OTHER PUBLICATIONS

Victores et al., "Robot-aided tunnel inspection and maintenance system by vision and proximity sensor integration," 2011, Automation in Construction, vol. 20, pp. 629-636.*

Avdelidis et al., "The technology of composite patches and their structural reliabliity inspection using infrared imaging," 2003, Progress in Aerospace Sciences, vol. 39, pp. 317-328.*

X. E. E Gros, "ABayesian statistical inference approach to the non-destructive inspection of composite material," 1996, NDT Data Fusion, pp. 95-126, XI-XIII.*

(Continued)

*Primary Examiner* — Kiho Kim
(74) *Attorney, Agent, or Firm* — Yee & Associates, P.C.

(57) ABSTRACT

A method and apparatus for inspecting a composite structure. A resin inspection system comprises a housing having an open section, a movement system associated with the housing, a light source associated with the housing, an infrared measurement system associated with the interior of the housing, and a visible light sensor system. The movement system is configured to move the housing on a surface of a composite structure. The light source is configured to emit light. The infrared measurement system is configured to generate infrared measurement information from infrared light detected by the infrared measurement system through the open section. The visible light sensor system is configured to generate image information about the surface of the composite structure.

20 Claims, 19 Drawing Sheets

(56) References Cited

OTHER PUBLICATIONS

Puri et al., "Indigenous development of miniature underwater radiation resistant CCTV camera for remotised inspection of coolant channels of PHWRS," 2004 BARC Newsletter, Issue No. 249, pp. 1-7.*

Related U.S. Appl. No. 13/151,147, filed Jun. 1, 2011, 25 Pages.

USPTO Notice of Allowance, dated Aug. 15, 2012, regarding U.S. Appl. No. 13/151,147, 8 pages.

* cited by examiner

FIG. 18

| 1802 | 1804 | 1806 | 1808 | 1810 | 1812 | 1814 | 1816 | 1818 | 1820 | 1822 |
|---|---|---|---|---|---|---|---|---|---|---|
| UPPER/ LOWER | SPAR | FRONT/ REAR | DEFECT TYPE | DISTANCE | WIDTH | DEPTH | LENGTH | LOCATION OF DEFECT | INFRARED IMAGE | VIDEO CAMERA IMAGE |
| UPPER 1824 | FS | REAR | POCKET | -7.9 | 0.16 | 15.5 | 12.3 | FLANGE | 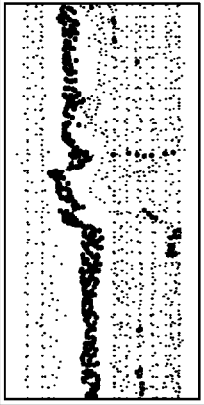 | |
| UPPER | FS | REAR | RIDGE | 30.7 | 0.96 | 10.7 | 8.5 | FLANGE | | |
| UPPER | FS | FRONT | POCKET | -4.3 | 0.08 | 14.1 | 6.6 | FLANGE | | |
| UPPER | FS | FRONT | POCKET | 98.6 | 0.30 | 9.3 | 14.8 | FLANGE | | |
| UPPER | FS | FRONT | POCKET | 183.3 | 0.12 | 14.8 | 14.1 | FLANGE | | |
| UPPER | FS | FRONT | POCKET | 320.6 | 0.08 | 15.3 | 3.2 | RADIUS | | |
| UPPER | M1 | REAR | RIDGE | 3.6 | 0.35 | 11.0 | 6.2 | MEMBER | | |
| UPPER | M1 | REAR | RIDGE | 51.7 | 0.12 | 4.9 | 5.3 | MEMBER | 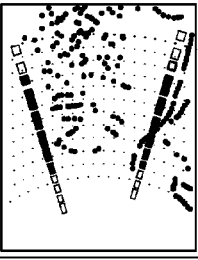 | 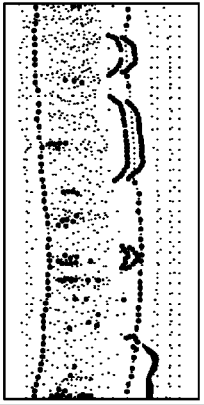 |
| UPPER | M1 | REAR | RIDGE | 71.6 | 0.12 | 6.2 | 10.7 | MEMBER | | |
| UPPER | M1 | REAR | RIDGE | 113.7 | 0.12 | 5.5 | 3.1 | MEMBER | | |
| UPPER | M1 | REAR | RIDGE | 334.0 | 0.11 | 11.4 | 62.7 | FLANGE | | |

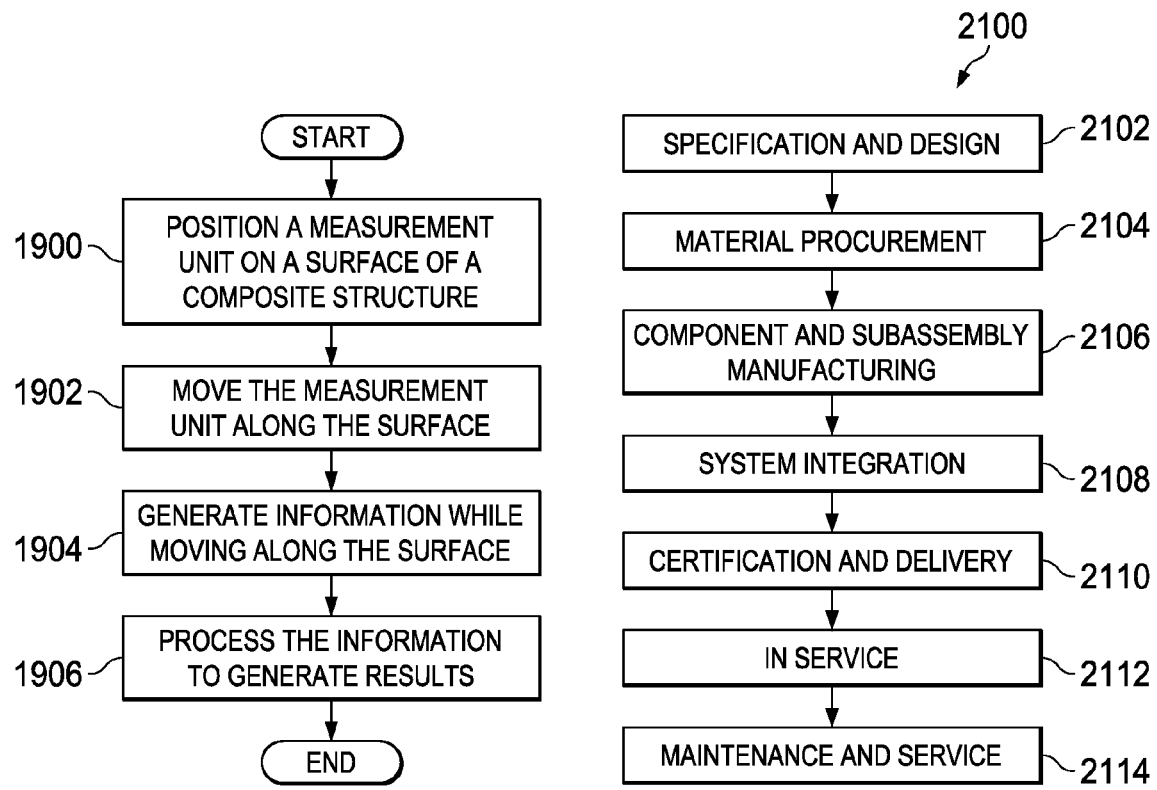
FIG. 19
FIG. 21
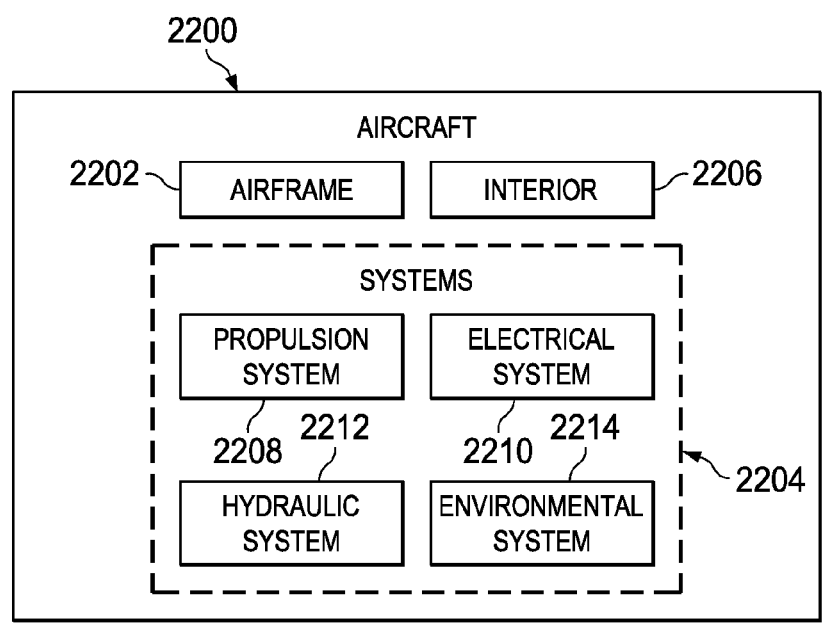
FIG. 22

FIG. 20
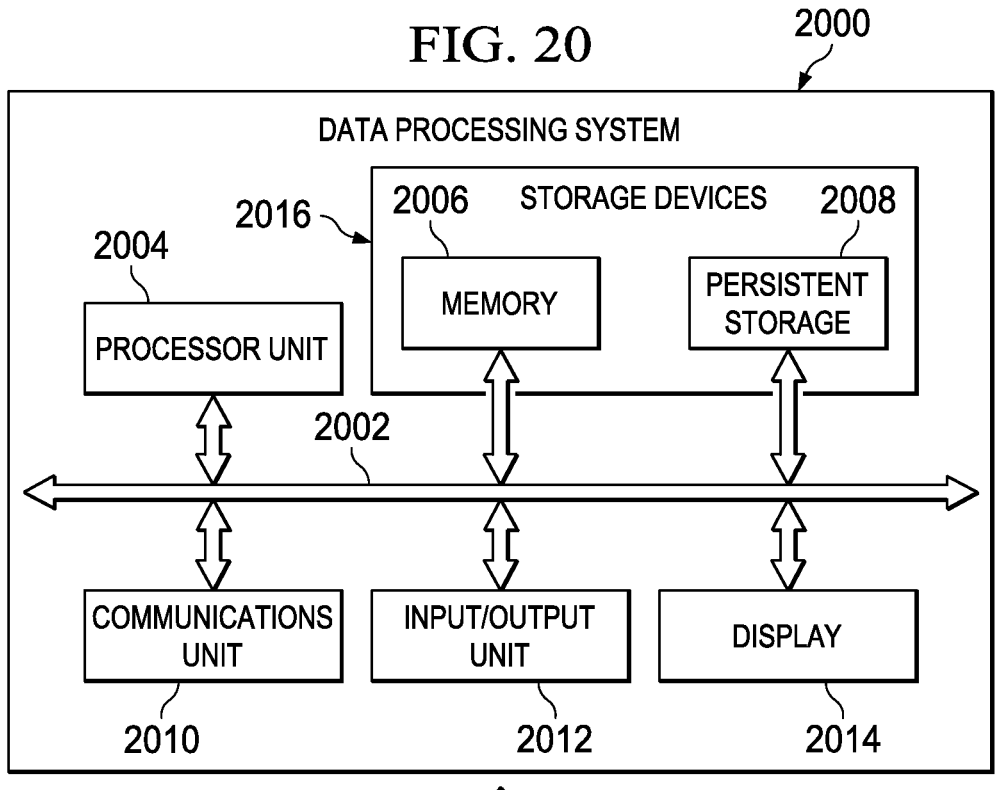
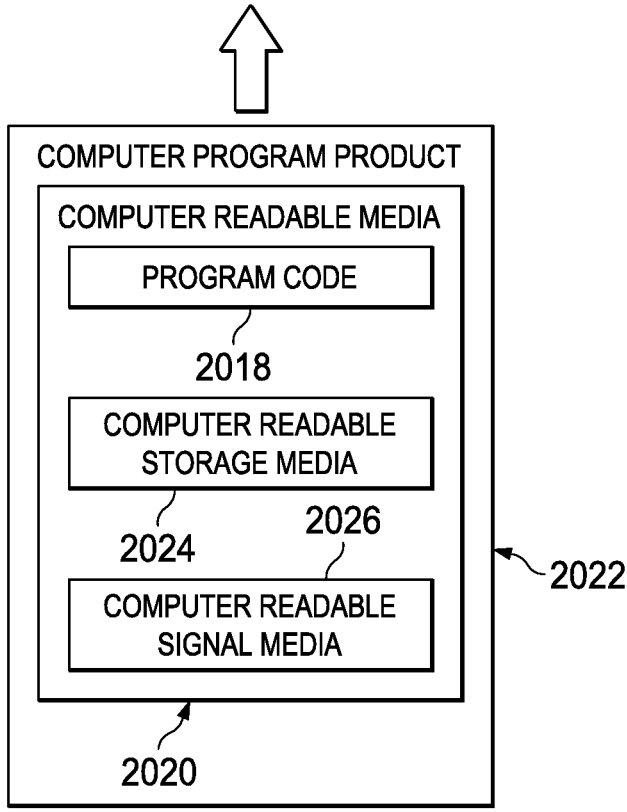

RESIN DETECTION SYSTEM

CROSS-REFERENCE TO RELATED APPLICATION

This application is related to U.S. patent application Ser. No. 13/151,147, filed Jun. 1, 2011, entitled "System and Method for Resin Thickness Measurement", which is incorporated herein by reference.

BACKGROUND INFORMATION

1. Field

The present disclosure relates generally to composite structures and, in particular, to inspecting composite structures. Still more particularly, the present disclosure relates to a method and apparatus for quantifying and characterizing resin on a composite structure.

2. Background

Composite structures are generally comprised of layers of resin-infused fiber. The layers of fiber may take the form of cloth, tape, or other suitable forms. The resin may already be infused in these layers or added while the layers are laid up to form the composite structure.

In fabricating composite structures with these types of layers, an inconsistency in the manner in which a layer is laid up with respect to other layers may result in an undesirable feature in the composite structure. For example, a wrinkle in one layer of fiber may propagate to other layers all the way to the surface of the composite structure. This propagation may form a depression in the surface of the structure. Resin may fill this depression during curing of the layers. This situation may result in a region in which the resin is thicker than in other areas. This type of region may be referred to as a pocket or a resin pocket.

Inspection of composite structures may be performed using non-destructive techniques (NDT). These techniques may include the use of ultrasonic systems. These types of systems, however, may not provide an ability to detect regions of resin containing an undesired thickness. For example, ultrasonic systems may be useful in detecting regions of resin that are over about 40 mils. However, for regions less than about 40 mils, the accuracy of the measurements may be lower than desired and make the measurements unreliable.

Therefore, it would be desirable to have a method and apparatus that takes into account the issues discussed above as well as possibly other issues.

SUMMARY

In one illustrative embodiment, a resin inspection system comprises a housing having an open section, a movement system associated with the housing, a light source associated with the housing, an infrared measurement system associated with an interior of the housing, and a visible light sensor system. The movement system is configured to move the housing on a surface of a composite structure. The light source is configured to emit light. The infrared measurement system is configured to generate infrared measurement information from infrared light detected by the infrared measurement system through the open section. The visible light sensor system is configured to generate image information about the surface of the composite structure.

In another illustrative embodiment, an apparatus comprises a housing, a movement system associated with the housing, and an infrared measurement system associated with an interior of the housing. The movement system is configured to move the housing on a surface of a composite structure. The infrared measurement system is configured to generate infrared measurement information in response to detecting infrared light reflected from the composite structure.

In yet another illustrative embodiment, a method for inspecting a composite structure is present. A measurement unit is moved on a surface of the inside of a cavity of a composite structure. Infrared measurement information is generated about the surface while moving on the surface of the inside of the cavity of the composite structure using an infrared measurement system in the measurement unit. A determination is made as to whether a region of resin is present from the infrared measurement information using a computer system.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and features thereof will best be understood by reference to the following detailed description of an illustrative embodiment of the present disclosure when read in conjunction with the accompanying drawings, wherein:

FIG. 18 is an illustration of an inconsistency report in accordance with an illustrative embodiment;

FIG. 19 is an illustration of a flowchart of a process for inspecting a composite structure in accordance with an illustrative embodiment;

FIG. 20 is an illustration of a data processing system in accordance with an illustrative embodiment;

FIG. 21 is an illustration of an aircraft manufacturing and service method in accordance with an illustrative embodiment; and FIG. 22 is an illustration of an aircraft in which an illustrative embodiment may be implemented.

DETAILED DESCRIPTION

The illustrative embodiments recognize and take into account one or more different considerations. For example, the illustrative embodiments recognize and take into account that one factor increasing the difficulty of detecting regions of resin during an inspection of a composite structure is limited access to different portions of the composite structure where inspection is desired.

For example, if the composite structure has cavities in which inspections are desired, currently used ultrasonic detection systems may not be able to reach those areas as easily as desired. Further, the configuration of some surfaces in these internal locations may make it more difficult to perform inspections.

For example, a composite structure may have two composite parts in which the composite parts are substantially parallel to each other and additional parts may be present that extend in a direction perpendicular to the two opposing composite parts. A joint is formed at the location where these composite parts intersect each other. This joint has a surface on which inspections may be performed. The surface may be curved and referred to as a radius for the joint.

Resin pockets or other types of regions in which resin is present may be undesirable within the composite structure for a desired level of performance. The performance of composite structure may be reduced to an undesirable level, depending on the amount of resin in these regions.

Further, one or more illustrative embodiments also recognize and take into account that visual inspections of the interior of composite structures may be more difficult than desired. In some cases, the size of the cavities may be such that a human operator is unable to look inside and determine whether a region of resin is a ridge or a pocket. A ridge is a region of resin that is raised on the composite structure. This situation is in contrast to a situation in which a pocket in a region is present. A ridge may not affect performance in the same manner as a pocket of resin.

Thus, one or more illustrative embodiments provide a method and apparatus for inspecting composite structures. In one illustrative embodiment, an apparatus comprises a housing, an infrared measurement system, and a movement system. The housing has an open section. The infrared measurement system is associated with the interior of the housing. The infrared measurement system is configured to generate data from infrared light detected by the infrared measurement system through the open section. The movement system is configured to move the housing on a surface.

Figure 1:
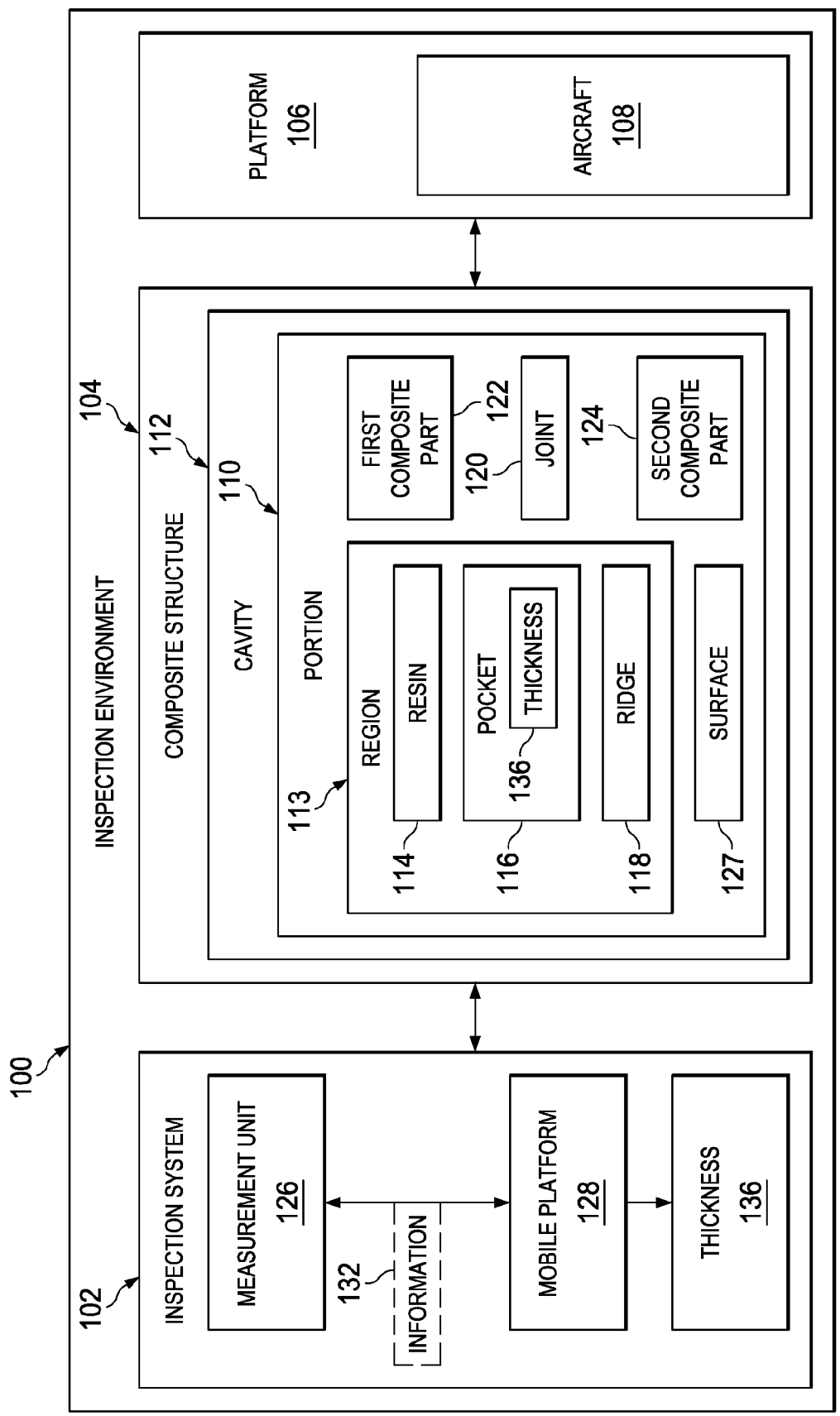
FIG. 1 is an illustration of a block diagram of an inspection environment in accordance with an illustrative embodiment.

With reference now to the figures and, in particular, with reference to FIG. 1, an illustration of a block diagram of an inspection environment is depicted in accordance with an illustrative embodiment. As depicted, inspection environment 100 includes inspection system 102, which may be used to perform inspections on composite structure 104. In these illustrative examples, composite structure 104 may be inspected outside of platform 106 or in its location within platform 106. In this illustrative example, platform 106 takes the form of aircraft 108. In these illustrative examples, inspection system 102 may be used to inspect portion 110 located within cavity 112 of composite structure 104.

In these illustrative examples, inspection system 102 may identify region 113 of resin 114 located in portion 110 of cavity 112 of composite structure 104. In this illustrative example, region 113 of resin 114 may take different forms. For example, without limitation, region 113 of resin 114 may be pocket 116, ridge 118, or other forms of resin 114. As depicted, pocket 116 may be an area in which a depression is present in layers of fiber or other material in a substrate, such as a composite substrate, for composite structure 104. Resin 114 may fill this depression to form pocket 116. Ridge 118 is resin that has accumulated on the surface of a layer or layers of fiber to form a ridge.

In these illustrative examples, portion 110 of composite structure 104 may be joint 120 where first composite part 122 meets second composite part 124. In these illustrative examples, inspection system 102 comprises measurement unit 126 and mobile platform 128. Measurement unit 126 is in communication with mobile platform 128. In these illustrative examples, measurement unit 126 is physically connected to mobile platform 128. In other illustrative examples, measurement unit 126 may be wirelessly connected to mobile platform 128.

In this illustrative example, mobile platform 128 is configured to hold measurement unit 126 when measurement unit 126 is not in use. Further, mobile platform 128 also may provide power and send information to measurement unit 126. Additionally, mobile platform 128 may receive information from measurement unit 126.

In these illustrative examples, measurement unit 126 is configured to be placed into cavity 112 to perform inspections of portion 110 of composite structure 104. In particular, measurement unit 126 may move along surface 127 of portion 110 of joint 120 within cavity 112. The movement of measurement unit 126 may be automatic or controlled by mobile platform 128 in these illustrative examples.

With inspection system 102, information 132 about portion 110 of composite structure 104 may be generated. In particular, information 132 may include information about region 113 of resin 114 that may be present in portion 110. With information 132, a detection of region 113 of resin 114 may be made.

Further, information 132 may be used to determine whether region 113 of resin 114 is pocket 116, ridge 118, or some other type of region. In these illustrative examples, information 132 may be used to identify thickness 136 when pocket 116 is present in portion 110.

In this manner, a determination may be made as to whether composite structure 104 may have a desired level of performance using information 132. In particular, information 132 may be used to make a determination as to whether joint 120 has a desired level of performance based on whether region 113 of resin 114 is present and what form region 113 of resin 114 takes when region 113 is present.

Figure 2:
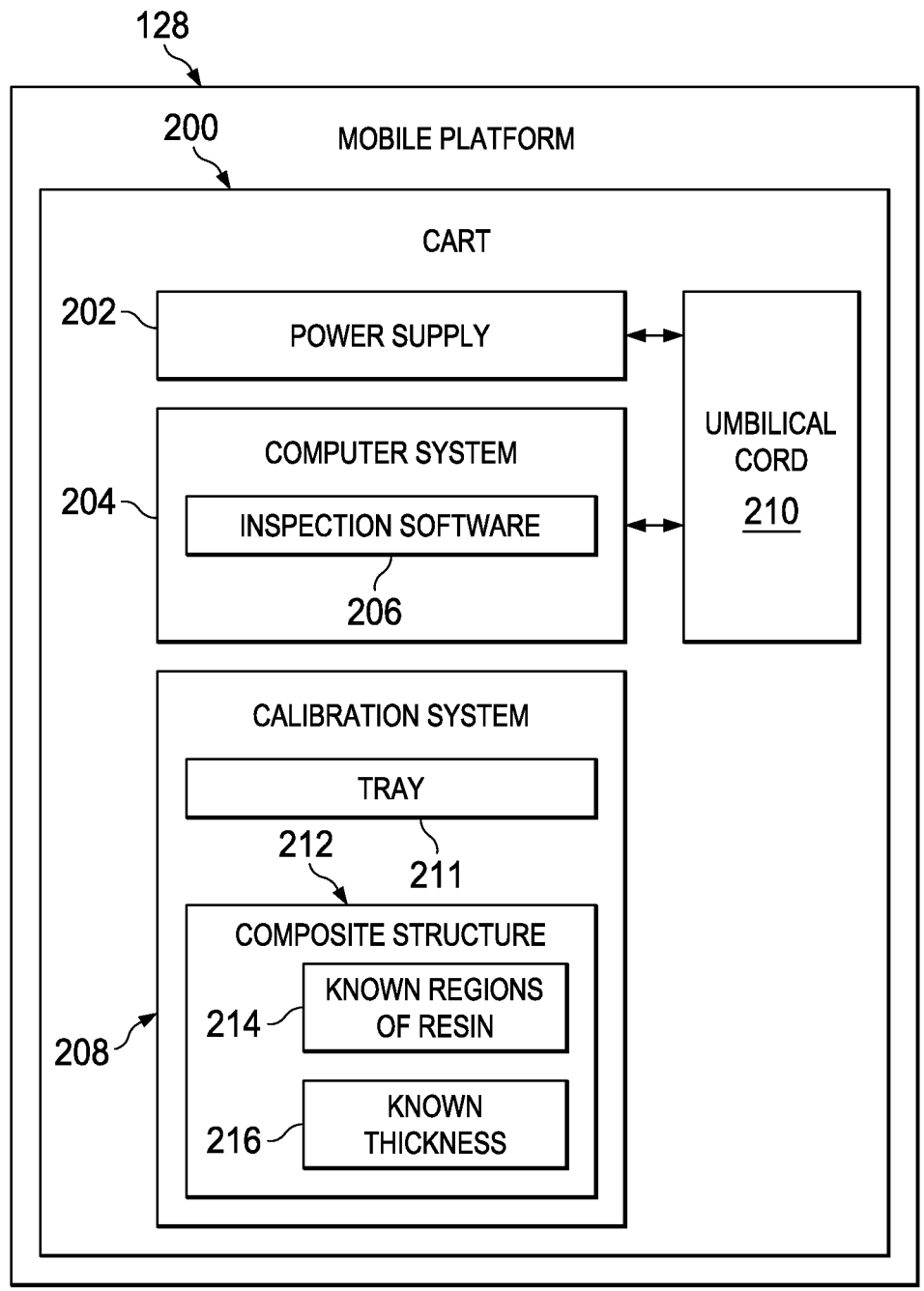
FIG. 2 is an illustration of a block diagram of a mobile platform in accordance with an illustrative embodiment.

Turning next to FIG. 2, an illustration of a block diagram of a mobile platform is depicted in accordance with an illustrative embodiment. In this depicted example, one implementation for mobile platform 128 is shown.

As depicted, mobile platform 128 includes cart 200. Cart 200 is moveable with respect to composite structure 104 in platform 106 in FIG. 1. In these illustrative examples, cart 200 is configured to carry components for mobile platform 128, such as power supply 202, computer system 204, inspection software 206, calibration system 208, umbilical cord 210, and other suitable components.

Power supply 202 is configured to supply power to measurement unit 126 in FIG. 1. Power supply 202 may be, for example, without limitation, a power converter, a battery, a generator, or some other suitable type of power supply.

Computer system 204 is one or more computers and may include displays, user input devices, and other components. When more than one computer is present in computer system 204, those computers may be in communication with each other.

Inspection software 206 is located in computer system 204 and is configured to receive data from measurement unit 126, analyze the data, generate reports, and perform other suitable operations. Further, inspection software 206 also may control the operation of measurement unit 126. For example, inspection software 206 may control movement of measurement unit 126.

As depicted, calibration system 208 is configured to be used in calibrating measurement unit 126. This calibration may be performed prior to measurement unit 126 being used to generate information 132 about portion 110 of composite structure 104 in FIG. 1. For example, without limitation, calibration system 208 may comprise tray 211 and composite structure 212. Composite structure 212 may be held in tray 211. Composite structure 212 has known regions of resin 214. These known regions of resin may have known thickness 216. Measurement unit 126 may be placed in tray 211 with composite structure 212, and calibration processes may be performed using composite structure 212. In this manner, measurement unit 126 may be calibrated such that measurement unit 126 provides information with a desired level of accuracy.

Umbilical cord 210 provides a connection between mobile platform 128 and measurement unit 126. Umbilical cord 210 may be one or more lines within a protective cover. Umbilical cord 210 is configured be connected to different components for mobile platform 128. These components include, for example, power supply 202 and computer system 204. Umbilical cord 210 is configured to provide power from power supply 202 to measurement unit 126. Further, umbilical cord 210 also may be connected to computer system 204 such that information may be exchanged between computer system 204 and measurement unit 126.

Figure 3:
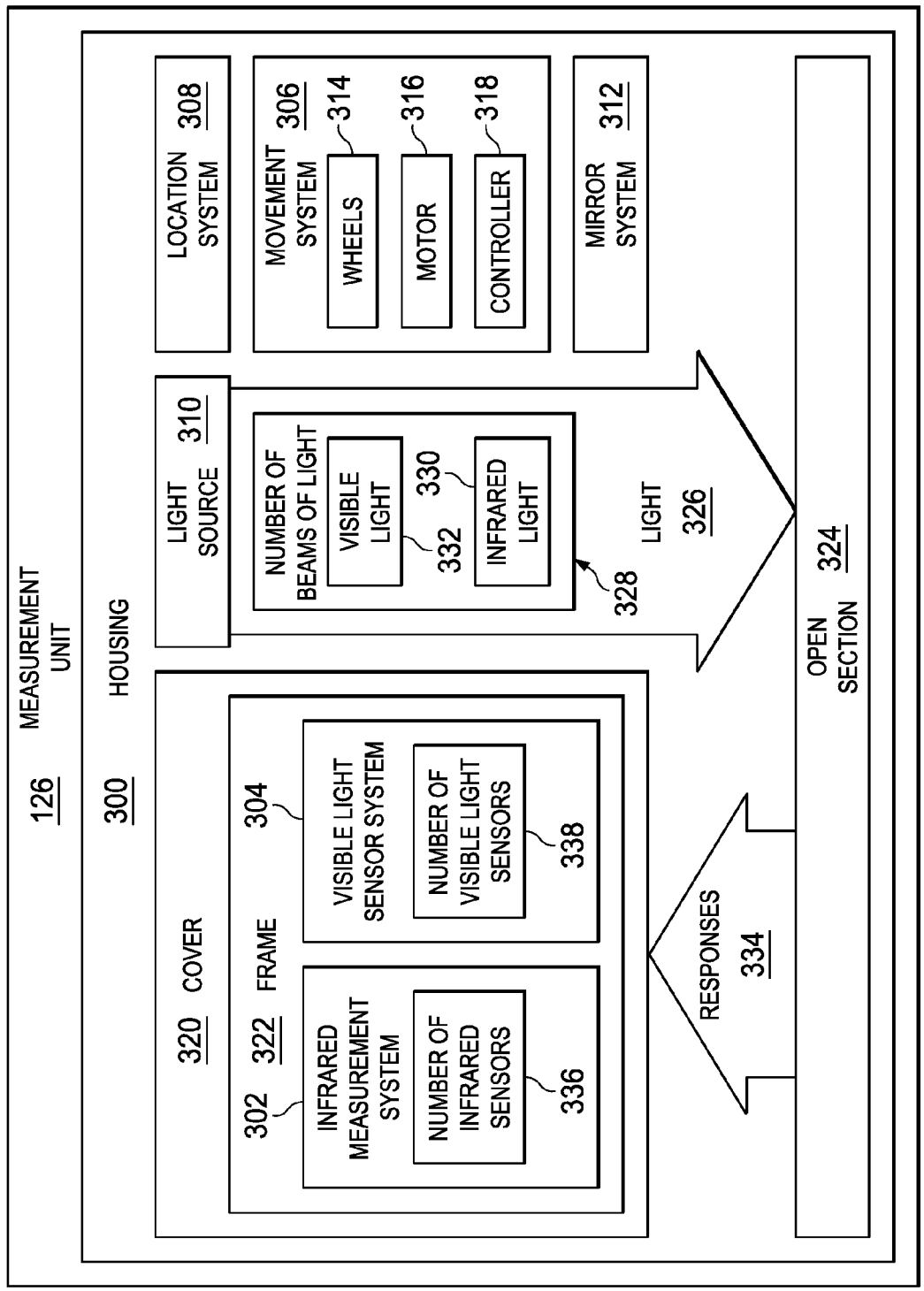
FIG. 3 is an illustration of a block diagram of a measurement unit in accordance with an illustrative embodiment.

Turning next to FIG. 3, an illustration of a block diagram of a measurement unit is depicted in accordance with an illustrative embodiment. An example of components from measurement unit 126 is depicted in this example.

Measurement unit 126 includes housing 300 in this illustrative example. Housing 300 has a shape and size configured for use in cavity 112 in FIG. 1 in these illustrative examples. Various components may be associated with housing 300. For example, infrared measurement system 302, visible light sensor system 304, movement system 306, location system 308, light source 310, mirror system 312, and other suitable components may be associated with housing 300.

In this illustrative example, infrared measurement system 302 and visible light sensor system 304 may be located within housing 300. Movement system 306 also may be located within housing 300 or, in some illustrative examples, may be associated with the exterior of housing 300.

Movement system 306 is configured to move housing 300 and other components for measurement unit 126 on surface 127 of portion 110 in cavity 112 of composite structure 104 in FIG. 1. In these illustrative examples, movement system 306 comprises wheels 314, motor 316, and controller 318. Motor 316 rotates wheels 314 under the control of controller 318. Controller 318 may be controlled by inspection software 206 in FIG. 2 in these illustrative examples.

In this illustrative example, housing 300 is comprised of cover 320 and frame 322. Housing 300 has open section 324. Open section 324 is configured to allow infrared measurement system 302 and visible light sensor system 304 to generate data about portion 110 in cavity 112 of composite structure 104 from within the interior of housing 300. In some illustrative examples, open section 324 may be covered by a transparent material that has desired optical properties for using infrared measurement system 302, visible light sensor system 304, and light source 310.

Light source 310 is configured to illuminate portion 110 of composite structure 104 within cavity 112 with light 326. Light source 310 may send light 326 to open section 324 in these depicted examples.

In these illustrative examples, light source 310 may emit light 326 in the form of number of beams of light 328. Number of beams of light 328 may have different wavelengths. For example, number of beams of light 328 may include at least one of infrared light 330, visible light 332, and other suitable types of light.

In some illustrative examples, a single beam of light in number of beams of light 328 may include light with various wavelengths. For example, a beam of light may include visible light 332, infrared light 330, and other wavelengths of light. A beam of light may have a single wavelength or a range of wavelengths, depending on the particular implementation. For example, a beam of light in number of beams of light 328 may include wavelengths for visible light 332, infrared light 330, and other wavelengths of light.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C.

Responses 334 to infrared light 330 may be detected by infrared measurement system 302. Responses 334 to visible light 332 also may be detected by visible light sensor system 304.

Infrared light 330 may have a wavelength from about 750 nanometers to about 100,000 nanometers. In these illustrative examples, wavelengths in a near-infrared portion of the infrared light spectrum may be used. This range may be from about 750 nanometers to about 2,500 nanometers. Of course, other wavelengths may be used, depending on the particular implementation.

Infrared measurement system 302 may be comprised of number of infrared sensors 336. In these illustrative examples, number of infrared sensors 336 may detect responses to infrared light 330 in light 326. Number of infrared sensors 336 may take a number of different forms. For example, number of infrared sensors 336 may be arranged in an array or grid. In these illustrative examples, number of infrared sensors 336 may correspond to one or more pixels. Number of infrared sensors 336 may be located in an infrared camera, a hyperspectral infrared imaging unit, and other suitable types of devices that detect infrared light 330.

Visible light sensor system 304 is comprised of number of visible light sensors 338 and is configured to detect visible light 332 reflected from portion 110 of composite structure 104 within cavity 112 in these illustrative examples. Number of visible light sensors 338 in visible light sensor system 304 may take a number of different forms. For example, number of visible light sensors 338 may be one or more cameras. These cameras may generate image information in various forms. The image information may be, for example, individual images, or it may generate a video stream, depending on the particular implementation.

Location system 308 is configured to identify a location of measurement unit 126. In this illustrative example, location system 308 may be, for example, an encoder system that is configured to identify how far measurement unit 126 has moved along surface 127.

Of course, location system 308 may take other forms. For example, without limitation, location system 308 may be a global positioning system receiver, an inertial measurement unit, or other suitable types of systems configured to provide information about the location of measurement unit 126.

Mirror system 312 is configured to adjust the view of infrared measurement system 302 and visible light sensor system 304 in the illustrative examples. Mirror system 312 may allow for infrared measurement system 302 and visible light sensor system 304 to be placed in different locations within housing 300 that may not be directly over open section 324 or pointed over open section 324.

Figure 4:
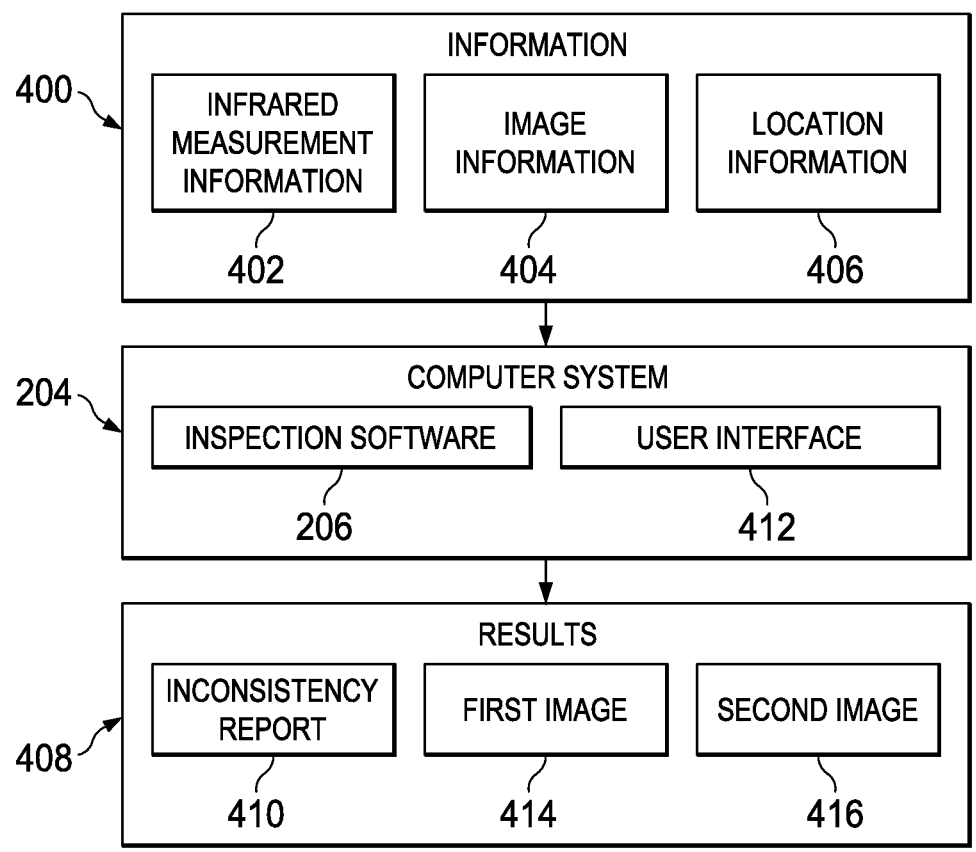
FIG. 4 is an illustration of a block diagram of the processing of information received from a measurement unit in accordance with an illustrative embodiment.

With reference now to FIG. 4, an illustration of a block diagram of the processing of information received from a measurement unit is depicted in accordance with an illustrative embodiment. In this illustrative example, inspection software 206 receives information 400 from measurement unit 126 in FIG. 1. In this illustrative example, information 400 includes infrared measurement information 402, image information 404, and location information 406.

Infrared measurement information 402 is received from infrared measurement system 302 in FIG. 3. Infrared measurement information 402 may include a thickness of resin in different locations as measured by infrared measurement system 302. For example, the wavelengths of infrared light detected by infrared measurement system 302 may indicate the thickness of the resin within a particular region.

In these examples, image information 404 is received from visible light sensor system 304 in FIG. 3. Image information 404 may be used to verify whether a region of resin is a pocket or a ridge.

Location information 406 is received from location system 308 in FIG. 3. Location information 406 may be used to correlate infrared measurement information 402, image information 404, and other suitable information with a particular location in portion 110 of composite structure 104.

Inspection software 206 processes at least one of infrared measurement information 402, image information 404, and location information 406 in information 400 to generate results 408. Results 408 may take a number of different forms. For example, results 408 may include inconsistency report 410. Inconsistency report 410 may identify locations where resin has been detected with a thickness greater than a threshold. Additionally, inconsistency report 410 also may include an indication as to whether a pocket or a ridge is present. Inconsistency report 410 may be displayed on user interface 412 on a display device in computer system 204.

Additionally, other information for results 408 may be generated and displayed on user interface 412. For example, inspection software 206 also may generate first image 414 and second image 416. First image 414 may be generated from infrared measurement information 402, and second image 416 is generated from image information 404.

First image 414 may indicate a thickness of resin. First image 414 may be used to identify a presence of region 113 of resin 114. In particular, first image 414 may be comprised of pixels in which colors are used to indicate a thickness of resin, and the location of the pixels in the image correspond to locations on portion 110 of composite structure 104.

Second image 416 may be used to determine whether the region of resin is a pocket or a ridge. Second image 416 may be in color or grayscale, depending on the particular implementation. Inspection software 206 may display first image 414 and second image 416 for a particular region of resin that has been identified.

The illustration of inspection environment 100 in FIG. 1 and the different components in FIGS. 1-4 are not meant to imply physical or architectural limitations to the manner in which an illustrative embodiment may be implementation. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, inspection system 102 may include one or more measurement units in addition to measurement unit 126 that are in communication with mobile platform 128. In still other illustrative examples, mobile platform 128 may take other forms other than cart 200. For example, mobile platform 128 may be a motorized vehicle, such as a truck or van.

In yet other illustrative examples, measurement unit 126 may omit visible light sensor system 304. In still other illustrative examples, housing 300 may take the form of a frame having many open sections. For example, housing 300 may have other open sections in addition to open section 324 used by light source 310 to project light onto portion 110 and used by infrared measurement system 302 and visible light sensor system 304 to detect responses 334 to light 326.

In yet other illustrative examples, umbilical cord 210 may be omitted. Instead, communication may be established between mobile platform 128 and measurement unit 126 through wireless connections. For example, wireless communications links may be used to exchange information between computer system 204 in mobile platform 128 and measurement unit 126. Power may be supplied to measurement unit 126 through wireless mechanisms, such as electromagnetic induction, electromagnetic radiation, microwaves, and other suitable mechanisms for transferring power. In yet another illustrative example, movement system 306 may include other types of locomotion other than wheels 314. For example, movement system 306 may use legs in addition to or in place of wheels 314.

Figure 5:
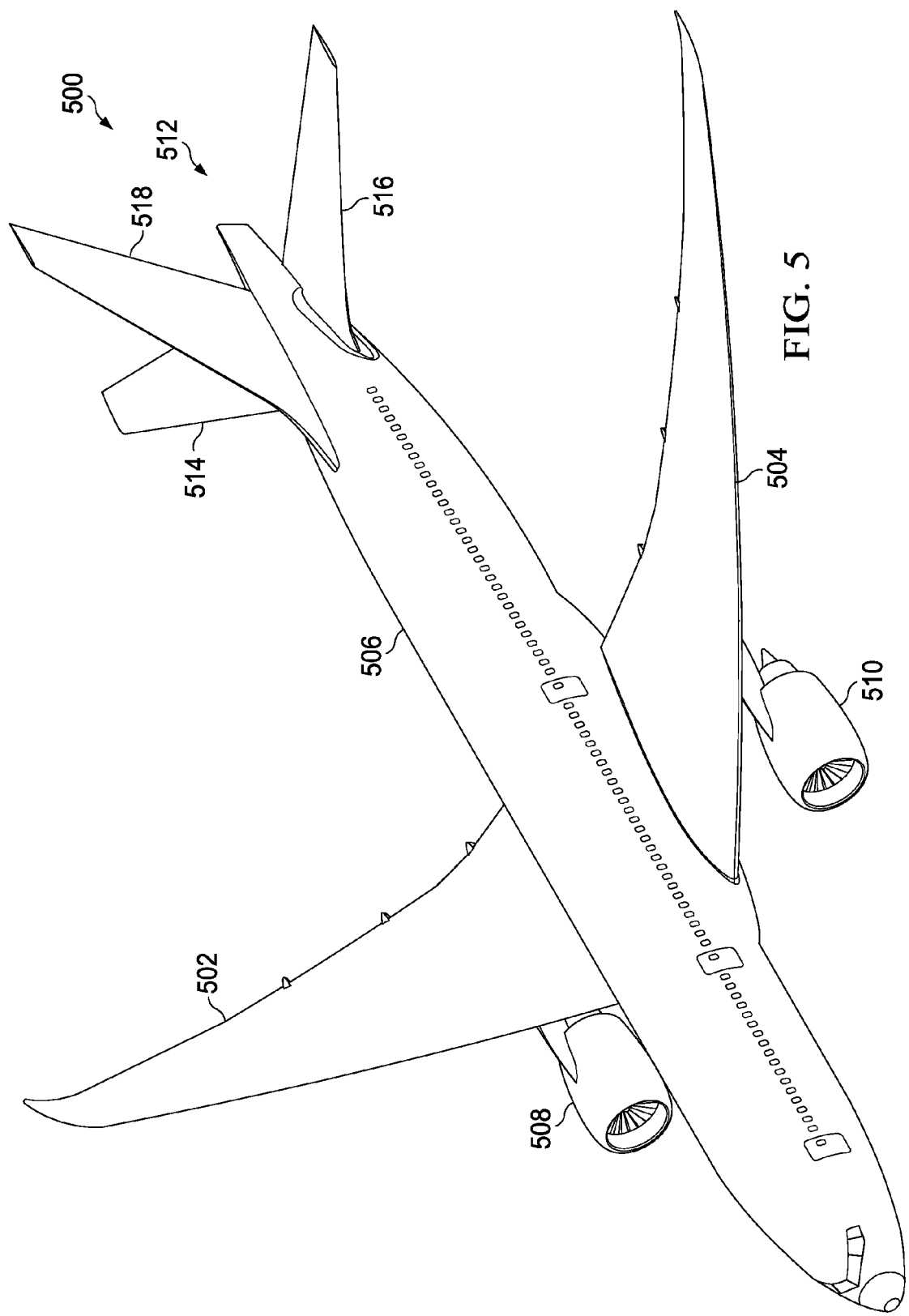
FIG. 5 is an illustration of a platform in which inspections may occur for regions of resin in accordance with an illustrative embodiment.

Turning next to FIG. 5, an illustration of a platform in which inspections may be made for regions of resin is depicted in accordance with an illustrative embodiment. In this illustrative example, aircraft 500 is one example of an implementation for aircraft 108 shown in block form in FIG. 1.

In this illustrative example, aircraft 500 has wing 502 and wing 504 attached to body 506. Aircraft 500 also includes engine 508 attached to wing 502 and engine 510 attached to wing 504. Body 506 has tail section 512. Horizontal stabilizer 514, horizontal stabilizer 516, and vertical stabilizer 518 are attached to body 506.

In these illustrative examples, composite structures within aircraft 500 may be inspected using inspection system 102 in FIG. 1. These composite structures may be inspected prior to the structures being assembled to form aircraft 500 or, in some cases, these structures may be inspected through access ports after assembly of aircraft 500.

Figure 6:
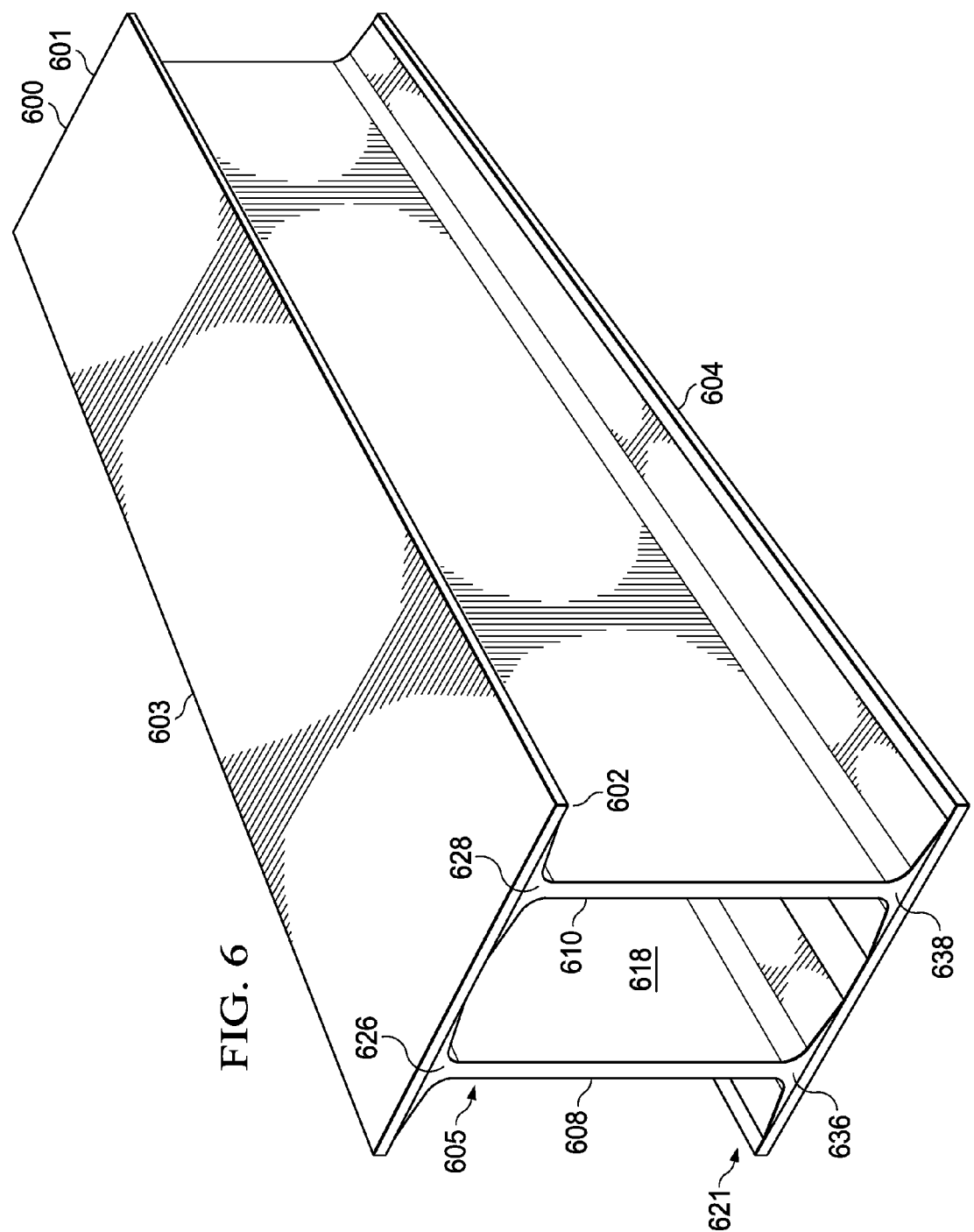
FIG. 6 is an illustration of a composite structure in which an inspection may be made for regions of resin in accordance with an illustrative embodiment.

Turning next to FIG. 6, an illustration of a composite structure in which an inspection may be made for regions of resin is depicted in accordance with an illustrative embodiment. In this illustrative example, composite structure 600 is a composite structure in aircraft 500 that may be inspected using inspection system 102 in FIG. 1.

In this illustrative example, composite structure 600 has end 601 and end 602. Composite structure 600 is comprised of first panel 603 and second panel 604, which are located opposite to each other. Composite structure 600 also includes members 605 connected to first panel 603 and second panel 604. In this example, members 605 comprises member 608 and member 610. Member 608, member 610, first panel 603, and second panel 604 are composite structures in these illustrative examples that form composite structure 600.

All of these parts for composite structure 600 are comprised of composite materials in this depicted example. In particular, these parts may be formed from layers of fibers infused with resin that has been cured. The assembly of the composite panels and members for composite structure 600 forms cavity 618. Cavity 618 may be referred to as a bay or cell within composite structure 600. In particular, inspections for regions of resin may be made at joints 621 located within cavity 618. In this example, joints 621 include joint 626, joint 628, joint 636, and joint 638.

Inspections of the surfaces of joints 621 may be more difficult than desired without the use of inspection system 102 in FIG. 1 for portions of joints 621 located within cavity 618. In these illustrative examples, the use of inspection system 102 reduces the difficulty of inspecting joints 621 within cavity 618. In particular, measurement unit 126 in FIG. 1 is configured to perform inspections of joints 621 within cavity 618.

Figure 7:
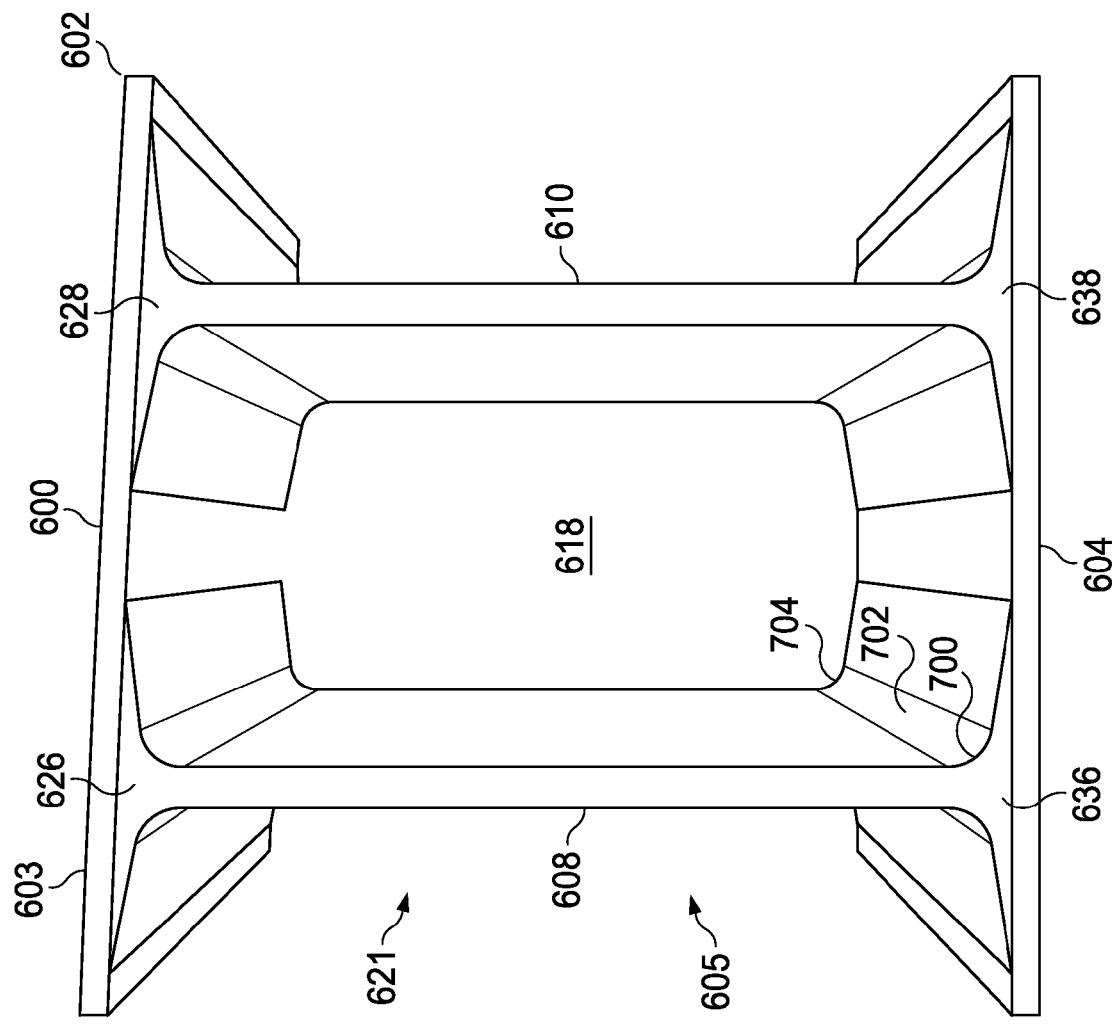
FIG. 7 is an illustration of a side view of a composite structure in accordance with an illustrative embodiment.

Turning next to FIG. 7, an illustration of a side view of a composite structure is depicted in accordance with an illustrative embodiment. In this depicted example, end 602 of composite structure 600 is depicted.

In this illustrative example, inspection of joints 621 in composite structure 600 may be made in accordance with an illustrative embodiment. A joint is a location at which two components are connected to each other. For example, joint 636 is a location where member 608 is connected to second panel 604.

In particular, these joints may be inspected to determine whether regions of resin are present at undesirable levels. In other words, a determination may be made as to whether a region of resin is present that is in the form of a pocket that has a thickness that is greater than desired for a particular desired performance of composite structure 600.

For example, inspection of surface 700 of joint 636 may be made to determine whether regions of resin in the form of pockets are present. These pockets may have an amount of resin that has an undesirable thickness that results in an undesired performance of composite structure 600. Surface 700 is curved surface 702 and may take the form of radius 704. Surface 700 and other surfaces for joint 636 and other joints in joints 621 may be inspected in accordance with an illustrative embodiment.

Figure 8:
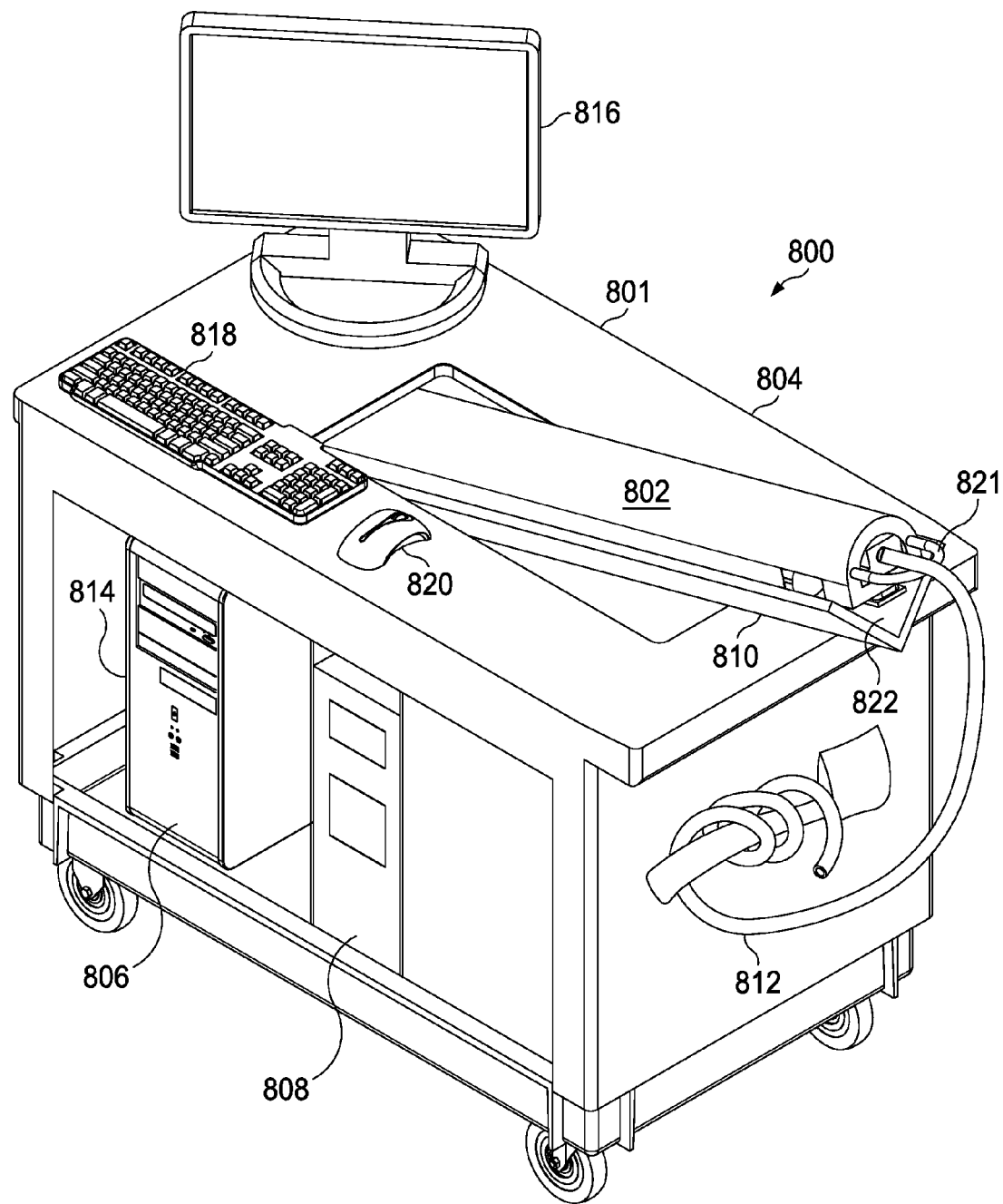
FIG. 8 is an illustration of an inspection system in accordance with an illustrative embodiment.

With reference now to FIG. 8, an illustration of an inspection system is depicted in accordance with an illustrative embodiment. Inspection system 800 is an example of a physical implementation for inspection system 102 shown in block form in FIGS. 1-4.

As depicted, inspection system 800 comprises mobile platform 801 and measurement unit 802. As depicted, mobile platform 801 takes the form of cart 804. Components, such as computer system 806, power supply 808, calibration system 810, and umbilical cord 812 may be associated with cart 804.

When one component is "associated" with another component, the association is a physical association in these depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

As can be seen, computer system 806 is comprised of multiple components. For example, computer system 806 includes computer 814, display device 816, keyboard 818, and mouse 820.

In this illustrative example, power supply 808 is configured to be connected to a power source. Power supply 808 provides power with a desired voltage and current to various components, such as computer system 806 and measurement unit 802. In these illustrative examples, umbilical cord 812 connects various components in cart 804 to measurement unit 802.

Calibration system 810 is comprised of tray 821 and composite structure 822. Composite structure 822 is located in tray 821 and has known properties that may be used to calibrate the data generated by measurement unit 802. Further, tray 821 in calibration system 810 also may serve as a structure to hold measurement unit 802 when measurement unit 802 is not in use.

Figure 9:
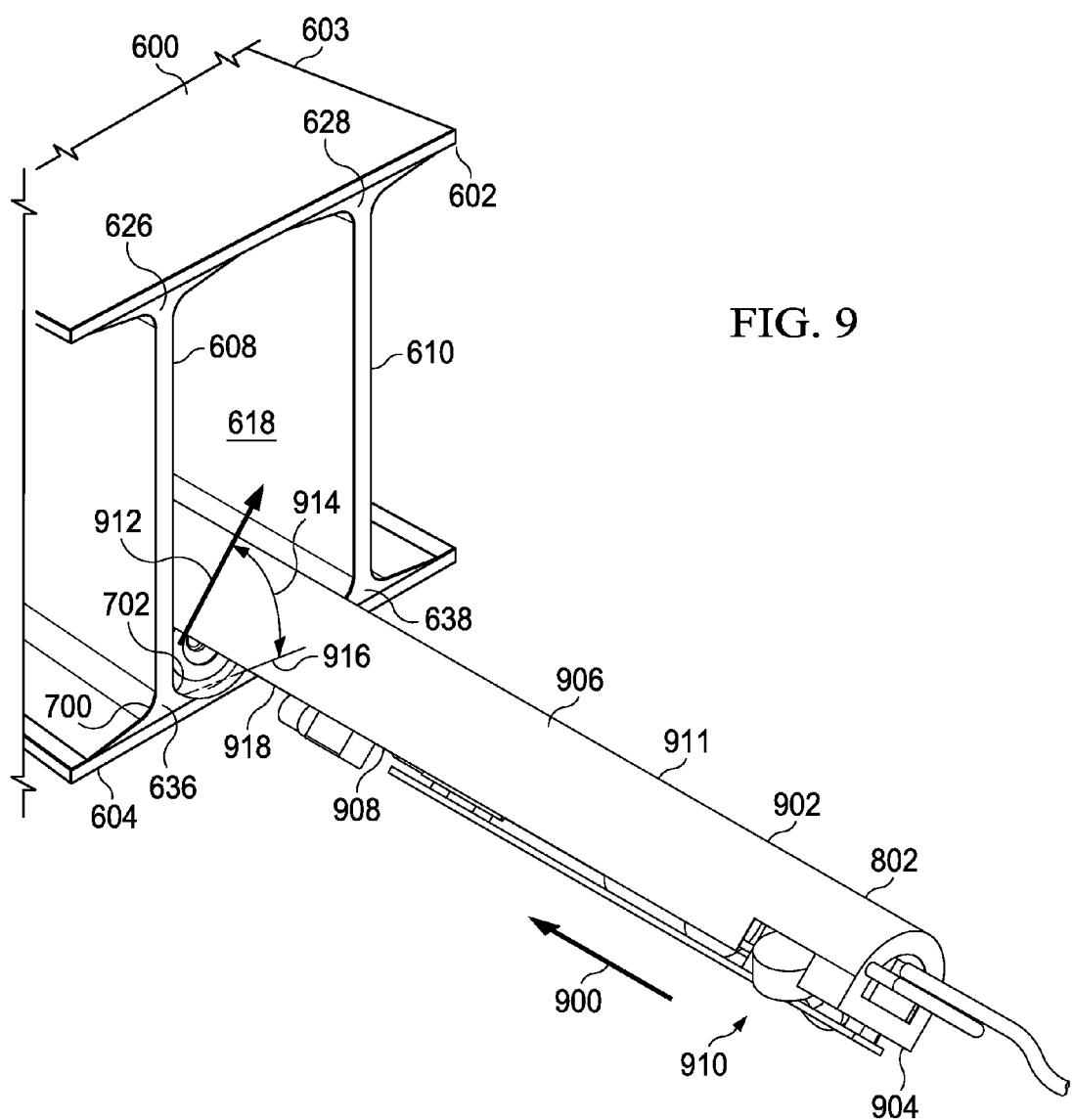
FIG. 9 is an illustration of a measurement unit in a composite structure in accordance with an illustrative embodiment.

With reference now to FIG. 9, an illustration of a measurement unit in a composite structure is depicted in accordance with an illustrative embodiment. In this illustrative example, measurement unit 802 has been placed into cavity 618. Measurement unit 802 is configured to move in the direction of arrow 900 into cavity 618 of composite structure 600.

In this illustrative example, measurement unit 802 generates data about resin that may be present on surface 700 of joint 636 as measurement unit 802 moves on surface 700 within cavity 618. As can be seen, measurement unit 802 is comprised of housing 902. Housing 902 comprises frame 904 and cover 906. Housing 902 has open section 908 that provides components within housing 902 exposure to surface 700 to make measurements in determining whether regions of resin are present.

As can be seen in this illustrative example, bottom side 910 of measurement unit 802 is in contact with surface 700 of joint 636. In this illustrative example, top 911 of measurement unit 802 has an orientation in the direction of arrow 912.

This orientation has angle 914. Angle 914 is an angle between arrow 912 and plane 916. Plane 916 is substantially planar to surface 918 of second panel 604. In the depicted examples, angle 914 is about 45 degrees. Of course, some other value for angle 914 may be used, depending on the particular implementation. For example, angle 914 may be about 40 degrees, about 60 degrees, or some other suitable angle, depending on surface 700 of joint 636 within cavity 618.

Figure 10:
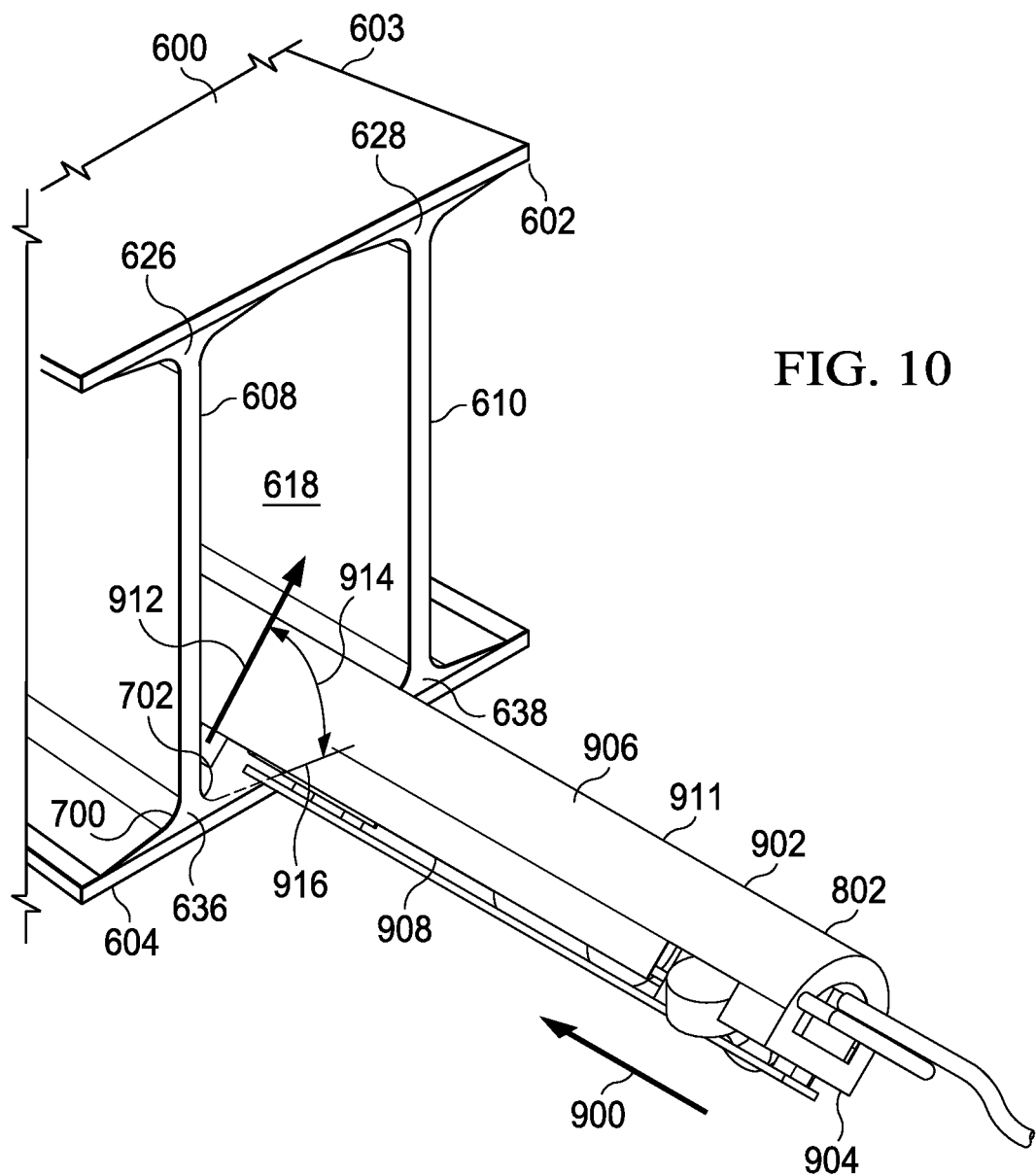
FIG. 10 is an illustration of a measurement unit moving into a cavity in a composite structure in accordance with an illustrative embodiment.

Turning next to FIG. 10, an illustration of a measurement unit moving into a cavity in a composite structure is depicted in accordance with an illustrative embodiment. As can be seen in this illustrative example, measurement unit 802 has moved farther into cavity 618. As measurement unit 802 moves into cavity 618 along surface 700, measurement unit 802 generates information about surface 700.

Figure 11:
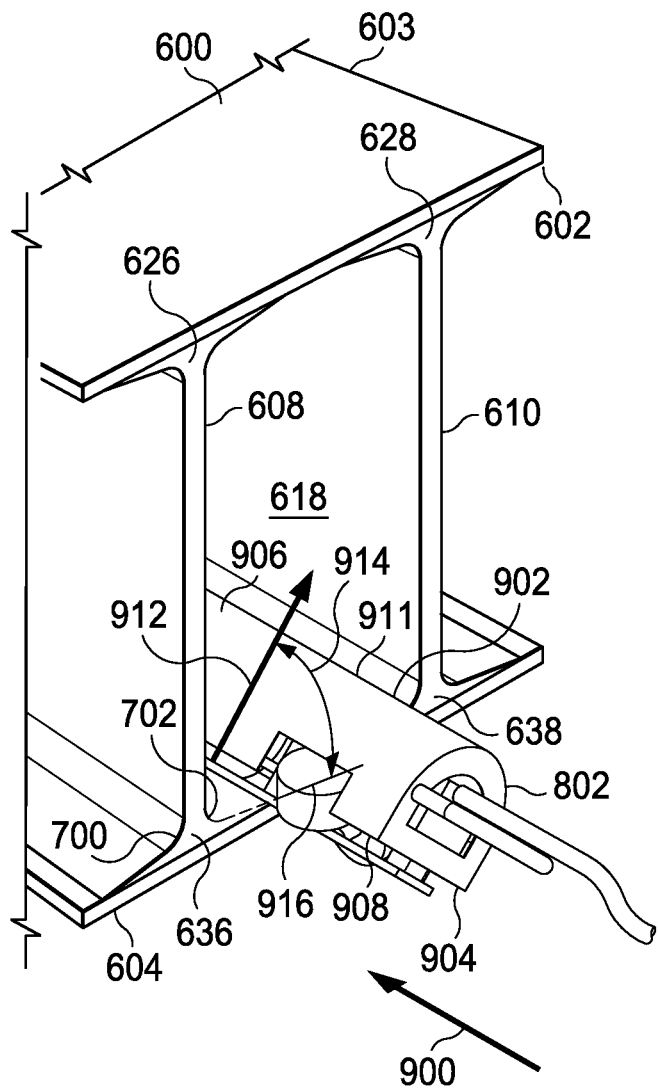
FIG. 11 is another illustration of a measurement unit moving into a cavity of a composite structure in accordance with an illustrative embodiment.

Turning next to FIG. 11, another illustration of a measurement unit moving into a cavity of a composite structure is depicted in accordance with an illustrative embodiment. In this example, measurement unit 802 has moved farther into cavity 618 in the direction of arrow 900. This movement with measurement unit 802 generating measurements and other information may continue until measurement unit 802 reaches end 601 (not shown) of composite structure 600.

The illustration of measurement unit 802 moving in the direction of arrow 900 through cavity 618 in composite structure 600 may be repeated for different joints within composite structure 600. Further, for joints, such as joint 626 and joint 628 shown in FIG. 6, composite structure 600 may be turned over such that measurement unit 802 may be moved along the surface of those joints to generate information about regions of resin that may be present on those joints.

Figure 12:
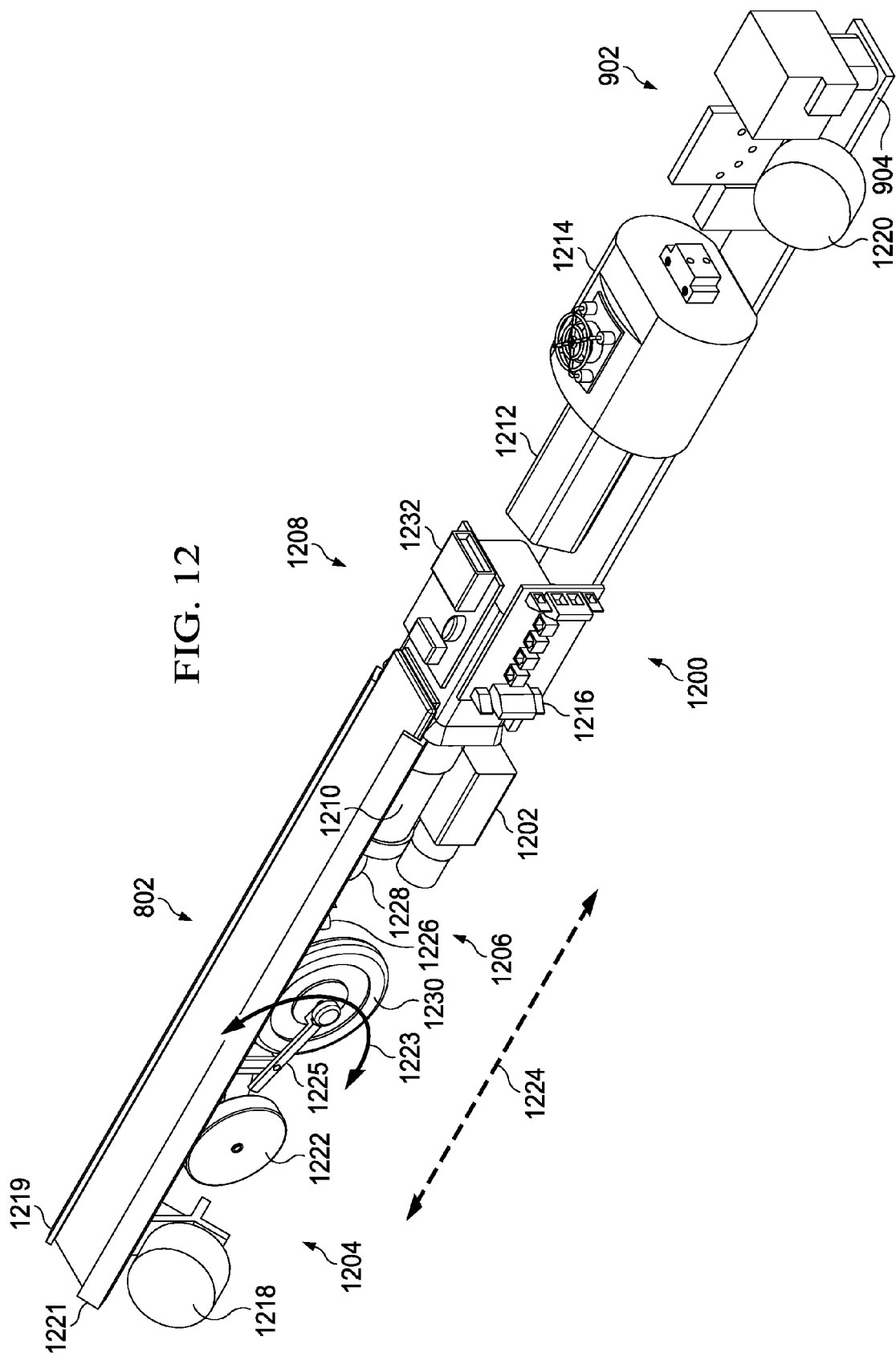
FIG. 12 is an illustration of components in a measurement unit in accordance with an illustrative embodiment.

With reference now to FIG. 12, an illustration of components in a measurement unit is depicted in accordance with an illustrative embodiment. In this illustrative example, measurement unit 802 is shown with cover 906 removed from housing 902. In this illustrative example, a number of different components are shown associated with frame 904 of housing 902.

As depicted, measurement unit 802 includes infrared measurement system 1200, visible light sensor system 1202, movement system 1204, light system 1206, and location system 1208.

In this illustrative example, infrared measurement system 1200 comprises focusing lens 1210, spectrometer 1212, and infrared camera 1214. In this illustrative example, visible light sensor system 1202 is comprised of visible light camera 1216.

Movement system 1204 includes front drive wheel 1218, rear drive wheel 1220, and guide wheel 1222 on side 1221. An additional front drive wheel is present on side 1219 opposite of front drive wheel 1218 but not seen in this view. Further, another rear drive wheel is present on side 1219 opposite of rear drive wheel 1220 but not seen in this view.

The configuration of these wheels in movement system 1204 is selected such that measurement unit 802 may be maintained such that top 911 has an orientation in the direction of arrow 912 as shown in FIGS. 9-11. This orientation is maintained while measurement unit 802 moves along surface 700 of joint 636.

Both front drive wheel 1218 and rear drive wheel 1220 are motorized wheels. Each of these wheels includes a motor that turns the wheels. Guide wheel 1222 is configured to help guide the movement of measurement unit 802 into cavity 618. Guide wheel 1222 is connected to structure 1225. Structure 1225 is configured to pivot in the direction of arrow 1223 about axis 1224. In these illustrative examples, the direction of arrow 1223 may be from side to side with respect to measurement unit 802. In these illustrative examples, axis 1224 extends through the interior of measurement unit 802. In this illustrative example, light system 1206 includes light source 1226. Light source 1226 emits a beam of light that includes both visible light and infrared light. In these illustrative examples, light source 1226 may be, for example, a number of halogen lights.

In this illustrative example, location system 1208 comprises encoder wheel 1230 and encoder electronics 1232. Encoder wheel 1230 is connected to structure 1225. Encoder wheel 1230 turns while measurement unit 802 moves within a cavity. Encoder electronics 1232 records the amount of movement of measurement unit 802 such that the position of measurement unit 802 can be identified. This location information may be used to identify where on surface 700 measurements of resin depth were made.

Further, encoder electronics 1232 also may act as a controller to control operation of movement system 1204. Further, encoder electronics 1232 also may control the generation of information by infrared measurement system 1200 and visible light sensor system 1202.

Figure 13:
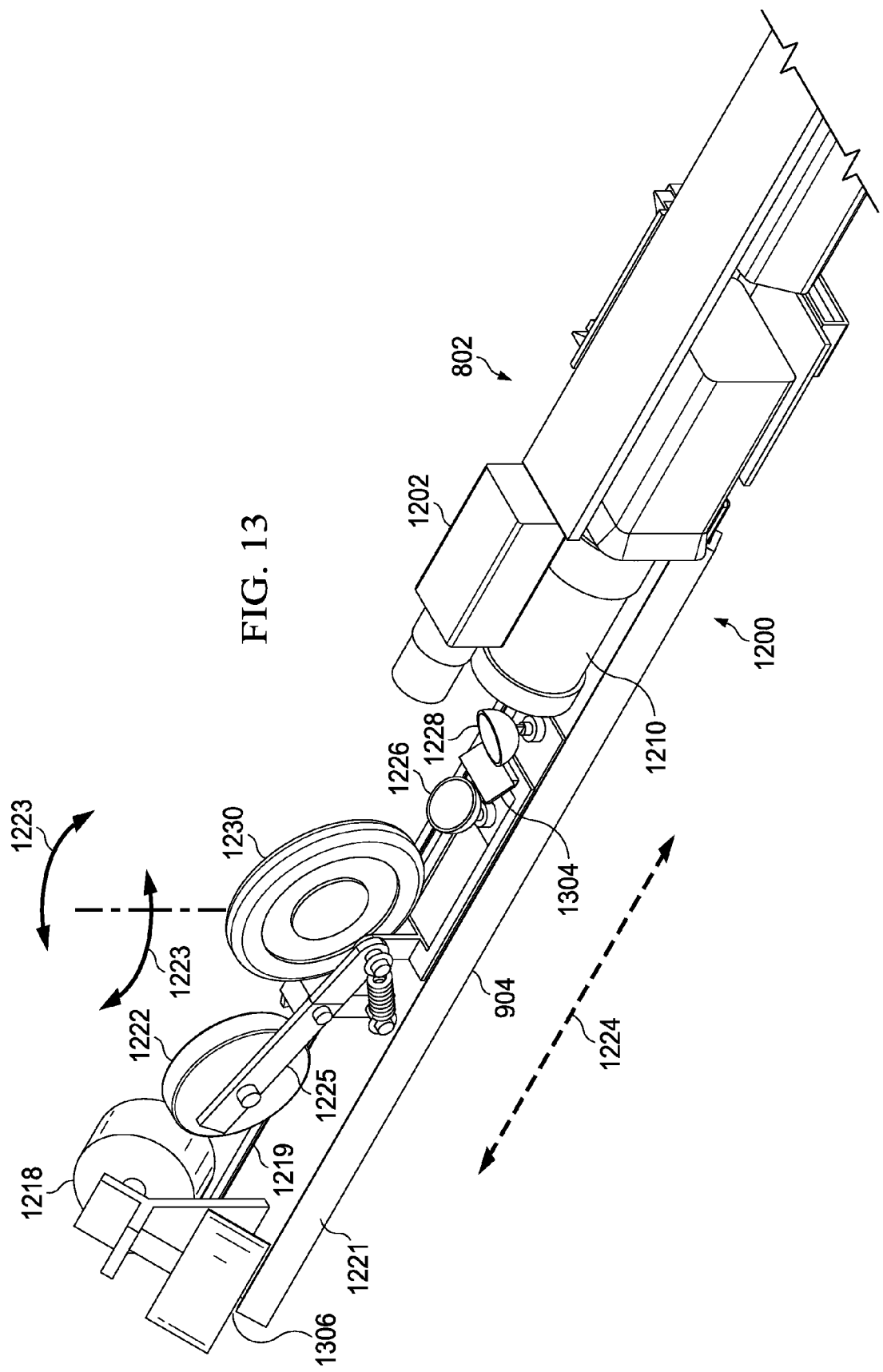
FIG. 13 is another view of a measurement unit in accordance with an illustrative embodiment.

Turning next to FIG. 13, another view of a measurement unit is depicted in accordance with an illustrative embodiment. In this illustrative example, guide wheel 1222 and encoder wheel 1230 are mounted to structure 1225. Additionally, mirror 1304 is also associated with structure 1225. Mirror 1304 is configured to reflect light from the surface of a joint toward infrared measurement system 1200 and visible light sensor system 1202. Mirror 1304 adjusts the view of infrared measurement system 1200 and visible light sensor system 1202. This view may be adjusted as guide wheel 1222 moves and causes structure 1225 to pivot in the direction of arrow 1223.

In this view, front drive wheel 1306 is shown on side 1219 of measurement unit 802. Front drive wheel 1306 also includes a motor to turn this wheel.

Figure 14:
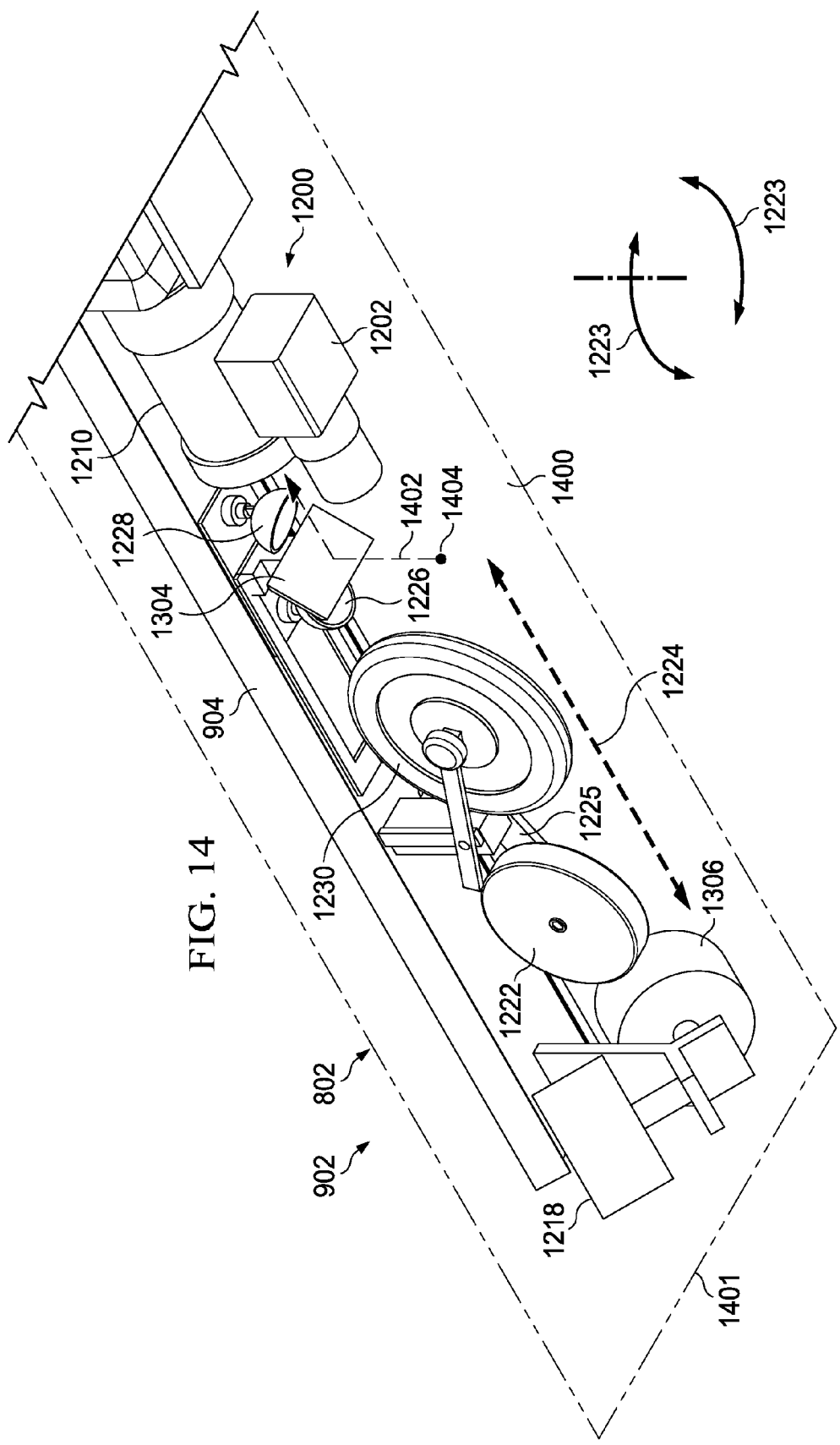
FIG. 14 is an illustration of light being directed to an infrared measurement system and a visible light sensor system in accordance with an illustrative embodiment.

Turning now to FIG. 14, an illustration of light being directed to an infrared measurement system and a visible light sensor system is depicted in accordance with an illustrative embodiment. In this illustrative example, a view of the bottom side of measurement unit 802 on surface 1400 of radius 1401 as seen through surface 1400 is depicted. Surface 1400 is shown as substantially transparent to illustrate the reflection of light from surface 1400.

As can be seen in this illustrative example, light reflected from surface 1400 is reflected by mirror 1304 in the direction of arrow 1402 towards infrared measurement system 1200 and visible light sensor system 1202. As can be seen in this illustrative example, light is reflected from location 1404 on surface 1400.

Structure 1225 pivots in the direction of arrow 1223 such that changes in the orientation of measurement unit 802 may not affect light received by infrared measurement system 1200 and visible light sensor system 1202.

In other words, light is reflected from location 1404 towards infrared measurement system 1200 and visible light sensor system 1202 even through the orientation of measurement unit 802 may change about axis 1224. The desired alignment of light reflected by mirror 1304 is directed by guide wheel 1222, because guide wheel 1222 maintains contact with surface 1400 and the guide wheel stays centered in radius 1401 while being measured. In this manner, more accurate measurements may be made with guide wheel 1222, structure 1225, and mirror 1304 as compared to mounting mirror 1304 to a fixed structure in measurement unit 802.

In other words, guide wheel 1222 causes structure 1225 to move such that mirror 1304 pivots in the direction of arrow 1223 to maintain mirror 1304 pointed at location 1404 even though measurement unit 802 may change orientations. In this manner, mirror 1304 may be maintained pointed at location 1404 on surface 1400 of a structure, such as a radius of a joint.

For example, guide wheel 1222 is configured to pivot as the shape of surface 1400. For example, when surface 1400 is the surface of the panel, the panel changes the angle between the panel and the member. While moving on surface 1400, measurement unit 802 may roll from side to side a bit as bumps and flange edges are encountered in the structure. However, guide wheel 1222 may move to maintain mirror 1304 in a position that is pointed towards surface 1400 at radius 1401.

The different components shown in FIGS. 5-14 may be combined with components in FIGS. 1-4, used with components in FIGS. 1-4, or a combination of the two. Additionally, some of the components in FIGS. 5-14 may be illustrative examples of how components shown in block form in FIGS. 1-4 can be implemented as physical structures.

Figure 15:
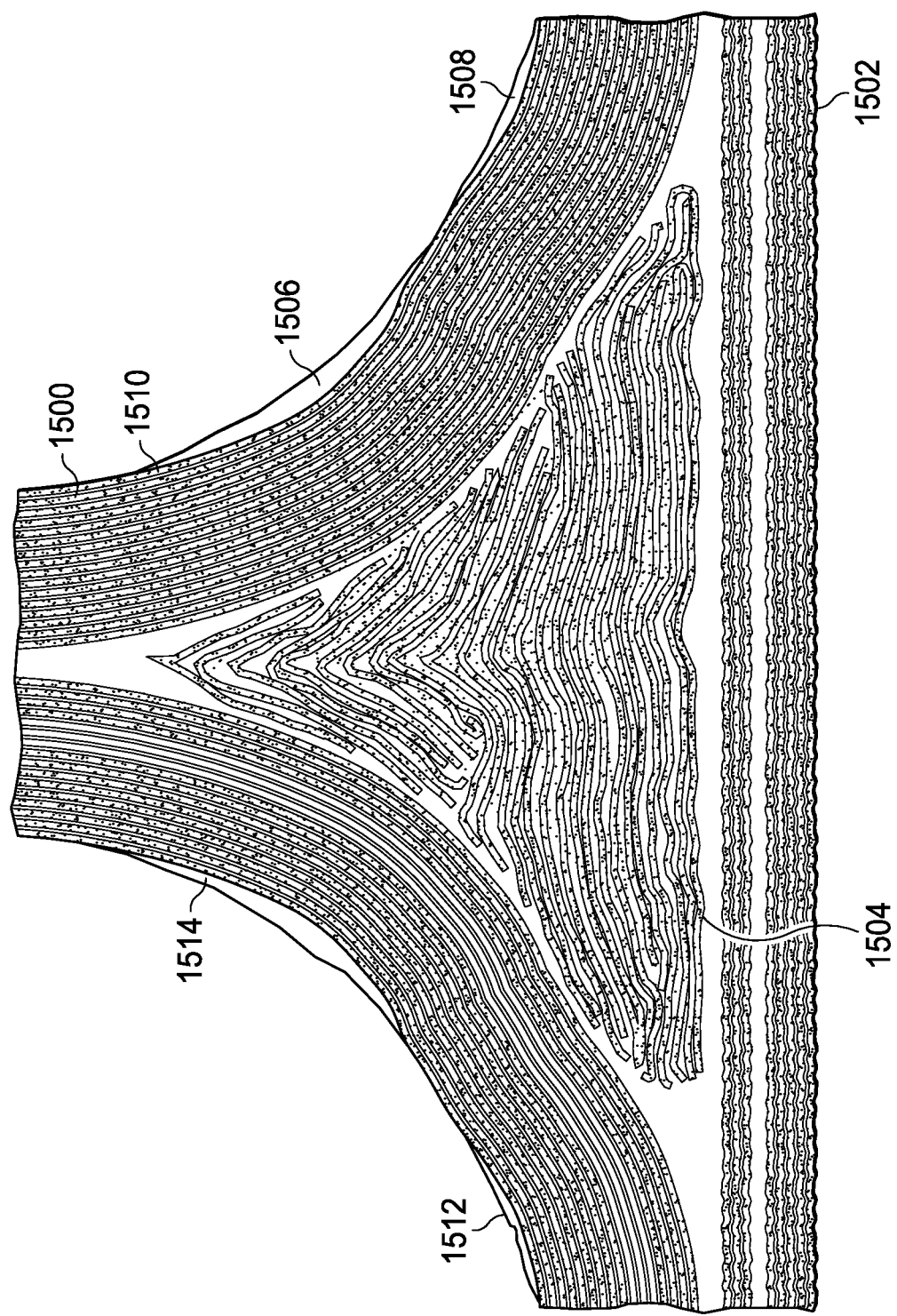
FIG. 15 is an illustration of a cross section of a joint in a composite structure in accordance with an illustrative embodiment.

Turning next to FIG. 15, an illustration of a cross section of a joint in a composite structure is depicted in accordance with an illustrative embodiment. In this illustrative example, member 1500 is seen connected to panel 1502 at joint 1504. These components are examples of components that may be found in aircraft 500 in FIG. 5. As depicted, resin is present in region 1506 and region 1508 on first side 1510 of joint 1504. Resin is also seen in region 1512 on second side 1514 of joint 1504.

Figure 16:
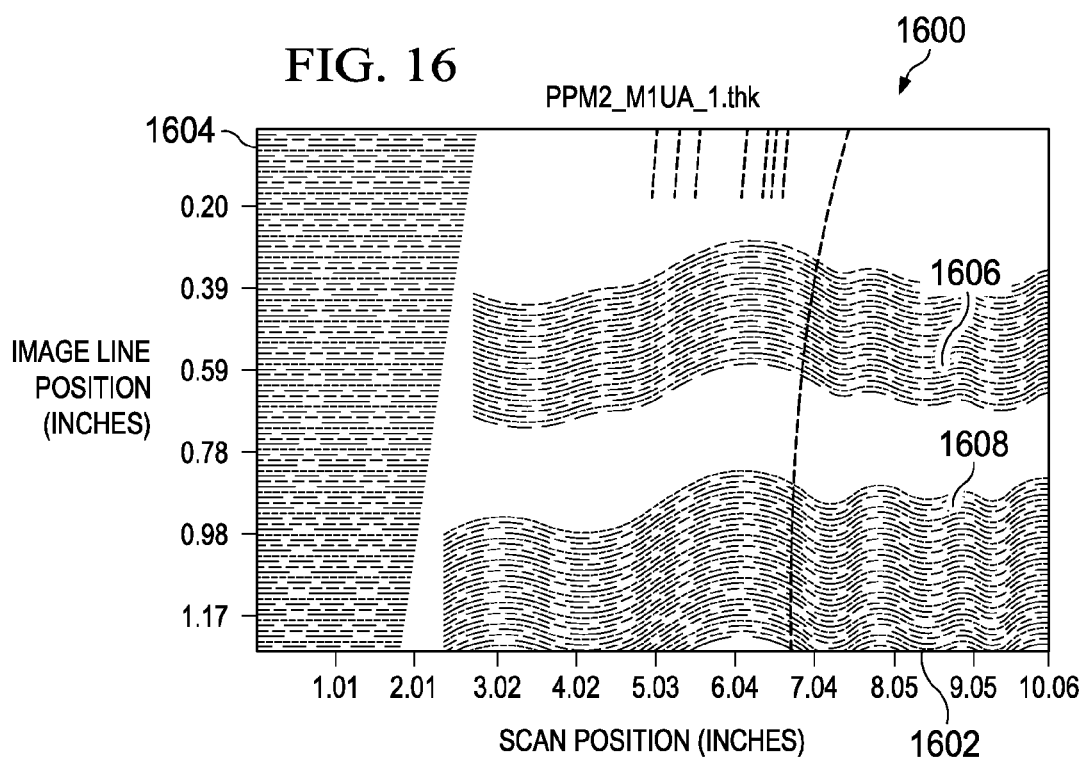
FIG. 16 is an illustration of a near IR image of the radius of a joint in accordance with an illustrative embodiment.

With reference now to FIG. 16, an illustration of a near IR image of the radius of a joint is depicted in accordance with an illustrative embodiment. In this illustrative example, image 1600 is an example of first image 414 that may be generated by inspection software 206 from infrared measurement information 402 in FIG. 4 generated by infrared measurement system 302 in FIG. 3. In this illustrative example, image 1600 corresponds to measurements of first side 1510 in FIG. 15 taken by an inspection system, such as inspection system 102 in FIG. 1.

X-axis 1602 represents the distance along joint 1504 in FIG. 15. In particular, this distance is the distance lengthwise extending through the cavity. Y-axis 1604 represents the width of joint 1504 that can be seen by the infrared measurement system.

Section 1606 and section 1608 indicate a presence of resin in these illustrative examples. Section 1606 corresponds to region 1506 in FIG. 15, and section 1608 corresponds to region 1508 in FIG. 15. The thickness of the resin may be indicated using colors, different levels of grayscale, or other suitable indicators.

Although illustrated as a two-dimensional image, image 1600 may be displayed in a three-dimensional form, depending on the particular implementation. In the illustrative examples, image 1600 also may be used to determine whether the resin in section 1606 and section 1608 are pockets of resin or ridges of resin. Typically, a pocket of resin may be broader and longer than a ridge of resin. Further, a pocket of resin also may have more of a bowl or oval shape as compared to a ridge.

The confirmation of whether section 1606 and section 1608 is a pocket of resin or a ridge of resin also may be made through an image using visible light sensor system 304 in FIG. 3. If these two regions of resin were ridges instead of pockets, the areas would show up as being lighter than the rest of the joint. The lighter color for ridges of resin occurs, because the height causes more reflectivity of the resin as compared to a pocket of resin in these illustrative examples.

Figure 17:
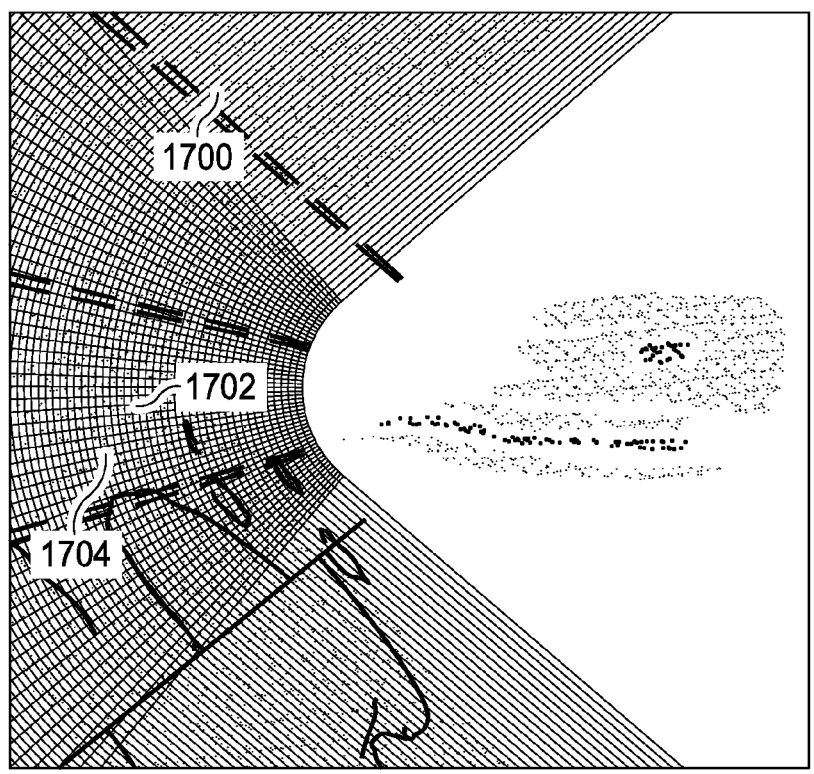
FIG. 17 is an illustration of a visible light image of a joint in accordance with an illustrative embodiment.

With reference now to FIG. 17, an illustration of a visible light image of a joint is depicted in accordance with an illustrative embodiment. Image 1700 is an example of second image 416 that may be generated by inspection software 206 from image information 404 in FIG. 4 generated by visible light sensor system 304 in FIG. 3.

In this example, image 1700 corresponds to the same location on a joint as image 1600 in FIG. 16. In this illustrative example, pocket 1702 and pocket 1704 are shown as darker lines along the radius of joint 1504 in FIG. 15. Image 1700 may be used to confirm that the resin is a pocket of resin instead of a ridge of resin.

In some cases, the presence of resin as indicated in section 1606 and section 1608 does not provide an ability to determine whether the resin is a ridge of resin or a pocket of resin. Image 1700 may be used to determine whether a region of resin identified in image 1600 is a ridge or a pocket.

With reference next to FIG. 18, an illustration of an inconsistency report is depicted in accordance with an illustrative embodiment. In this illustrative example, inconsistency report 1800 is an example of one manner in which inconsistency report 410 shown in block form in FIG. 4 may be implemented. In this illustrative example, inconsistency report 1800 includes columns 1802, 1804, 1806, 1808, 1810, 1812, 1814, 1816, 1818, 1820, and 1822.

As depicted, columns 1802, 1804, and 1806 identify a location of the measurements. For example, column 1802 indicates whether the measurement was taken on an upper or a lower portion of the member. Column 1804 in entry 1824 indicates a location of the member. For example, the location of the member may be front, middle, rear, or some other location. Column 1806 indicates the side of the member on which the measurement was taken. For example, the location may be forward or rear.

Column 1808 indicates the type of inconsistency. For example, the inconsistency may be a pocket of resin, a ridge of resin, or some other type of inconsistency. Column 1810 identifies a location of the inconsistency. In this illustrative example, the location may be a distance from the base or root of the member to the beginning of the inconsistency.

Columns 1812, 1814, and 1816 provide information about the dimensions of the inconsistency. In this illustrative example, column 1812 indicates a width of the inconsistency, column 1814 indicates a depth of the inconsistency, and column 1816 indicates a length of the inconsistency.

Column 1818 identifies a location of the inconsistency on the member. For example, column 1818 may indicate whether the inconsistency is on the radius, a flange next to the radius, or in some other location.

Column 1820 may include images of the inconsistency. Column 1820 may include images generated using an infrared measurement system, such as infrared measurement system 302 in FIG. 3. Column 1822 may include images generated using a visible light sensor system, such as visible light sensor system 304 in FIG. 3. In some cases, images may not be available in all entries.

The illustration of inconsistency report 1800 is not meant to limit the manner in which inconsistency reports may be generated. Other inconsistency reports may have other types of information in addition to or in place of the information illustrated in inconsistency report 1800. For example, in other reports, images may be excluded. Instead, links to images may be present in the report.

Turning now to FIG. 19, an illustration of a flowchart of a process for inspecting a composite structure is depicted in accordance with an illustrative embodiment. The process illustrated in FIG. 19 may be implemented in inspection environment 100 in FIG. 1. In particular, the process may be implemented in inspection system 102.

The process begins by positioning a measurement unit on a surface of a composite structure (operation 1900). In this illustrative example, the surface may be a surface of a joint in which the surface is located within the cavity of a composite structure in an aircraft.

The process then moves the measurement unit along the surface (operation 1902). This movement may be along the surface of a joint extending through a cavity in the composite structure. The measurement unit generates information while moving along the surface (operation 1904).

The information is processed to generate results (operation 1906), with the process terminating thereafter. The results may include an inconsistency report, images, and other suitable types of information. The images may be, for example, without limitation, images of resin thickness generated from measurements made by an infrared measurement system, images of the surface generated by a visible light sensor system, and other suitable types of images. This process may be repeated any number of times for different surfaces of the composite structure.

The flowchart and block diagrams in the different depicted embodiments illustrate the architecture, functionality, and operation of some possible implementations of apparatuses and methods in an illustrative embodiment. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowchart or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Turning now to FIG. 20, an illustration of a data processing system is depicted in accordance with an illustrative embodiment. Data processing system 2000 may be used to implement one or more computers in computer system 204 in FIG. 2. In this illustrative example, data processing system 2000 includes communications framework 2002, which provides communications between processor unit 2004, memory 2006, persistent storage 2008, communications unit 2010, input/output (I/O) unit 2012, and display 2014. In these examples, processor unit 2004 may be a bus system.

Processor unit 2004 serves to execute instructions for software that may be loaded into memory 2006. Processor unit 2004 may be a number of processors, a multi-processor core, or some other type of processor, depending on the particular implementation. "A number", as used herein with reference to an item, means one or more items. Further, processor unit 2004 may be implemented using a number of heterogeneous processor systems in which a main processor is present with secondary processors on a single chip. As another illustrative example, processor unit 2004 may be a symmetric multi-processor system containing multiple processors of the same type.

Memory 2006 and persistent storage 2008 are examples of storage devices 2016. A storage device is any piece of hardware that is capable of storing information, such as, for example, without limitation, data, program code in functional form, and/or other suitable information either on a temporary basis and/or a permanent basis. Storage devices 2016 may also be referred to as computer readable storage devices in these examples. Memory 2006, in these examples, may be, for example, a random access memory or any other suitable volatile or non-volatile storage device. Persistent storage 2008 may take various forms, depending on the particular implementation.

For example, persistent storage 2008 may contain one or more components or devices. For example, persistent storage 2008 may be a hard drive, a flash memory, a rewritable optical disk, a rewritable magnetic tape, or some combination of the above. The media used by persistent storage 2008 also may be removable. For example, a removable hard drive may be used for persistent storage 2008.

Communications unit 2010, in these examples, provides for communications with other data processing systems or devices. In these examples, communications unit 2010 is a network interface card. Communications unit 2010 may provide communications through the use of either or both physical and wireless communications links.

Input/output unit 2012 allows for input and output of data with other devices that may be connected to data processing system 2000. For example, input/output unit 2012 may provide a connection for user input through a keyboard, a mouse, and/or some other suitable input device. Further, input/output unit 2012 may send output to a printer. Display 2014 provides a mechanism to display information to a user.

Instructions for the operating system, applications, and/or programs may be located in storage devices 2016, which are in communication with processor unit 2004 through communications framework 2002. In these illustrative examples, the instructions are in a functional form on persistent storage 2008. These instructions may be loaded into memory 2006 for execution by processor unit 2004. The processes of the different embodiments may be performed by processor unit 2004 using computer implemented instructions, which may be located in a memory, such as memory 2006.

These instructions are referred to as program code, computer usable program code, or computer readable program code that may be read and executed by a processor in processor unit 2004. The program code in the different embodiments may be embodied on different physical or computer readable storage media, such as memory 2006 or persistent storage 2008.

Program code 2018 is located in a functional form on computer readable media 2020 that is selectively removable and may be loaded onto or transferred to data processing system 2000 for execution by processor unit 2004. Program code 2018 and computer readable media 2020 form computer program product 2022 in these examples. In one example, computer readable media 2020 may be computer readable storage media 2024 or computer readable signal media 2026.

Computer readable storage media 2024 may include, for example, an optical or magnetic disk that is inserted or placed into a drive or other device that is part of persistent storage 2008 for transfer onto a storage device, such as a hard drive, that is part of persistent storage 2008. Computer readable storage media 2024 also may take the form of a persistent storage, such as a hard drive, a thumb drive, or a flash memory, that is connected to data processing system 2000. In some instances, computer readable storage media 2024 may not be removable from data processing system 2000.

In these examples, computer readable storage media 2024 is a physical or tangible storage device used to store program code 2018 rather than a medium that propagates or transmits program code 2018. Computer readable storage media 2024 is also referred to as a computer readable tangible storage device or a computer readable physical storage device. In other words, computer readable storage media 2024 is a media that can be touched by a person.

Alternatively, program code 2018 may be transferred to data processing system 2000 using computer readable signal media 2026. Computer readable signal media 2026 may be, for example, a propagated data signal containing program code 2018. For example, computer readable signal media 2026 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 2018 may be downloaded over a network to persistent storage 2008 from another device or data processing system through computer readable signal media 2026 for use within data processing system 2000. For instance, program code stored in a computer readable storage medium in a server data processing system may be downloaded over a network from the server to data processing system 2000. The data processing system providing program code 2018 may be a server computer, a client computer, or some other device capable of storing and transmitting program code 2018.

The different components illustrated for data processing system 2000 are not meant to provide architectural limitations to the manner in which different embodiments may be implemented. The different illustrative embodiments may be implemented in a data processing system including components in addition to or in place of those illustrated for data processing system 2000. Other components shown in FIG. 20 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 2004 may take the form of a hardware unit that has circuits that are manufactured or configured for a particular use. This type of hardware may perform operations without needing program code to be loaded into a memory from a storage device to be configured to perform the operations.

For example, when processor unit 2004 takes the form of a hardware unit, processor unit 2004 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 2018 may be omitted, because the processes for the different embodiments are implemented in a hardware unit.

In still another illustrative example, processor unit 2004 may be implemented using a combination of processors found in computers and hardware units. Processor unit 2004 may have a number of hardware units and a number of processors that are configured to run program code 2018. With this depicted example, some of the processes may be implemented in the number of hardware units, while other processes may be implemented in the number of processors.

In another example, a bus system may be used to implement communications framework 2002 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of devices that transmit data, receive data, or transmit and receive data. A communications unit may be, for example, a modem or a network adapter, two network adapters, or some combination thereof. Further, a memory may be, for example, memory 2006, or a cache, such as found in an interface and memory controller hub that may be present in communications framework 2002.

Illustrative embodiments of the disclosure may be described in the context of aircraft manufacturing and service method 2100 as shown in FIG. 21 and aircraft 2200 as shown in FIG. 22. Turning first to FIG. 21, an illustration of an aircraft manufacturing and service method is depicted in accordance with an illustrative embodiment. During pre-production, aircraft manufacturing and service method 2100 may include specification and design 2102 of aircraft 2200 in FIG. 22 and material procurement 2104.

During production, component and subassembly manufacturing 2106 and system integration 2108 of aircraft 2200 takes place. Thereafter, aircraft 2200 may go through certification and delivery 2110 in order to be placed in service 2112. While in service 2112 by a customer, aircraft 2200 is scheduled for routine maintenance and service 2114, which may include modification, reconfiguration, refurbishment, and other maintenance or service.

Each of the processes of aircraft manufacturing and service method 2100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 22, an illustration of an aircraft is depicted in which an illustrative embodiment may be implemented. In this example, aircraft 2200 is produced by aircraft manufacturing and service method 2100 in FIG. 21 and may include airframe 2202 with plurality of systems 2204 and interior 2206. Examples of systems 2204 include one or more of propulsion system 2208, electrical system 2210, hydraulic system 2212, and environmental system 2214. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 2100 in FIG. 21. In one illustrative example, components or subassemblies produced in component and subassembly manufacturing 2106 in FIG. 21 may be fabricated or manufactured in a manner similar to components or subassemblies produced while aircraft 2200 is in service 2112. As yet another example, one or more apparatus embodiments, method embodiments, or a combination thereof may be utilized during production stages, such as component and subassembly manufacturing 2106 and system integration 2108. For example, inspection system 102 may be used to inspect composite structure 104 after composite structure 104 in FIG. 1 has been manufactured but prior to being integrated into aircraft 2200.

One or more apparatus embodiments, method embodiments, or a combination thereof may be utilized while aircraft 2200 is in service 2112 and/or during maintenance and service 2114. Further, inspection system 102 may be used to perform inspections in cavities of composite structures through access ports that may be present during maintenance and service 2114.

The use of a number of the different illustrative embodiments may substantially expedite the assembly of and/or reduce the cost of aircraft 2200. For example, inspecting composite structures with one or more cavities using inspection system 102 may reduce the amount of time needed to perform inspections as compared to currently used systems.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. For example, although platform 106 has been describe as being aircraft 108, platform 106 may be applied to other types of platforms. For example, without limitation, other illustrative embodiments may be applied to a mobile platform, a stationary platform, a land-based structure, an aquatic-based structure, a space-based structure, and/or some other suitable platform. More specifically, the different illustrative embodiments may be applied to, for example, without limitation, a submarine, a bus, a personnel carrier, a tank, a train, an automobile, a spacecraft, a space station, a satellite, a surface ship, a power plant, a dam, a manufacturing facility, a building, and/or some other suitable platform.

Further, the illustrative embodiments may be applied to inspect curved surfaces at locations other than joints. The illustrative embodiments may be applied to surfaces that are flat, surfaces with a radius, and other types of surfaces. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A resin inspection system comprising:
    a housing having an open lower section and an enclosed upper section, the open lower section configured to allow access to a surface of a composite structure being measured, wherein the housing is associated with a light source configured to emit light;
    a processor configured to execute a movement system associated with the housing, wherein the movement system is configured to move the housing on the surface of the composite structure;
    the processor configured to execute an infrared measurement system associated with an interior of the housing, wherein the infrared measurement system is configured to generate infrared measurement information from infrared light detected by the infrared measurement system through the open section;
    the processor configured to execute a visible light sensor system associated with the interior of the housing and configured to generate image information about the surface of the composite structure; and
    a computer system in communication with the infrared measurement system, wherein the computer system is configured to receive the infrared measurement information generated by the infrared measurement system, identify a thickness of layers in the composite structure, determine whether a pocket of resin is present in the composite structure, and determine whether a ridge of resin is accumulating on the surface of the composite structure.

2. The resin inspection system of claim 1, wherein the composite structure is a joint in a cavity of a composite structure and wherein the movement system is configured to move the housing on a surface of the joint within the cavity of the composite structure.

3. The resin inspection system of claim 1 further comprising:
    the processor configured to execute a mirror system configured to adjust a view of at least one of the infrared measurement system and the visible light sensor system.

4. The resin inspection system of claim 1 further comprising:
    the processor configured to execute a location system configured to identify a location of the housing wherein the infrared measurement information and the image information are generated on the surface of the composite structure.

5. The resin inspection system of claim 4, wherein the location system comprises:
    an encoder system configured to measure a distance traveled by the housing while the infrared measurement information and the image information is generated.

6. The resin inspection system of claim 1, wherein the housing, the movement system associated with the housing, the light source, the infrared measurement system, and the visible light sensor system form a measurement unit and further comprising:
    a mobile platform; and
    a computer system associated with the mobile platform, wherein the computer system is in communication with the measurement unit and is configured to process the infrared measurement information and the image information received from the measurement unit.

7. The resin inspection system of claim 6 further comprising:
    the processor configured to execute a calibration system associated with the mobile platform, wherein the calibration system is configured to calibrate the measurement unit by detecting undesired levels of thickness of resin on the surface of the composite structure, said undesired levels of thickness of resin including ridges and pockets, wherein a ridge is formed by resin accumulating on the surface of the composite structure via layers of fiber and wherein a pocket is formed when resin fills a depression of the surface of the composite structure via layers of fiber.

8. The resin inspection system of claim 6 further comprising:
    an umbilical cord connecting the measurement unit to the computer system.

9. The resin inspection system of claim 1, wherein the housing has the open lower section configured to allow the infrared light to pass into the housing for detection by the infrared measurement system.

10. The resin inspection system of claim 1, wherein the infrared measurement system comprises at least two light sources for providing surface feature illumination, an infrared spectrometer, an infrared camera, at least one cooled detector, and a number of guide wheels configured to rotate an infrared turning minor toward the surface being measured.

11. The resin inspection system of claim 1, wherein at least one of the processor and the computer system is configured to execute inspection software configured to generate a first image and a second image, the first image generated from infrared measurement information and configured to indicate a thickness of the resin comprising of pixels, wherein differing colors are used to indicate the thickness of the resin and pixel location on the first image indicates location of the resin on the portions of the composite structure, and the second image generated from image information, the second image configured to determine whether the region of resin is a pocket or a ridge.

12. An apparatus comprising:
a housing;
a movement system associated with the housing, wherein the movement system is configured to move the housing on a surface of a composite structure;
an infrared measurement system associated with an interior of the housing, wherein the infrared measurement system is configured to generate infrared measurement information in response to one of detecting and absorbing infrared light reflected from the composite structure; and
a computer system in communication with the infrared measurement system, wherein the computer system is configured to receive the infrared measurement information generated by the infrared measurement system, identify a thickness of layers in the composite structure, determine whether a pocket of resin is present in the composite structure, and determine whether a ridge of resin is accumulating on the surface of the composite structure.

13. The apparatus of claim 12 further comprising:
a visible light sensor system configured to generate image information in response to light reflected from the composite structure.

14. The apparatus of claim 13 further comprising:
a mirror system configured to adjust a view of at least one of the infrared measurement system and the visible light sensor system.

15. The apparatus of claim 12, wherein in being configured to generate the infrared measurement information in response to one of detecting and absorbing the infrared light reflected from the composite structure, the near infrared measurement system is further configured to generate an image indicating a thickness of a resin, wherein the image is selected from one of a two-dimensional image and a three-dimensional image.

16. The apparatus of claim 12, wherein the housing includes an open section and wherein the infrared measurement system is configured to generate the infrared measurement information from the infrared light detected by the infrared measurement system through the open section.

17. The apparatus of claim 12, wherein the surface of the composite structure is a surface of a joint within a cavity within a composite structure.

18. A method for inspecting a composite structure, the method comprising:
moving, by a processor, a measurement unit on a surface of an inside of a cavity of the composite structure;
generating, by the processor, infrared measurement information about the surface while moving on the surface of the inside of the cavity of the composite structure using an infrared measurement system in the measurement unit;
determining, by the processor, whether a region of resin having an undesired thickness is present from the infrared measurement information using a computer system; and
determining, by the processor, whether the region of resin having an undesired thickness is a pocket.

19. The method of claim 18, further comprising:
responsive to a determination that the region of resin having an undesired thicknesss is not a pocket, determining, by the processor, whether the region of resin is a ridge.

20. The method of claim 18 further comprising:
generating, by the processor, an inconsistency report identifying locations where the resin is detected as containing a region with an undesired thickness.

* * * * *